United States Patent
Hawkins

(10) Patent No.: US 11,020,135 B1
(45) Date of Patent: Jun. 1, 2021

(54) SHOCK WAVE DEVICE FOR TREATING VASCULAR PLAQUES

(71) Applicant: SHOCKWAVE MEDICAL, INC., Fremont, CA (US)

(72) Inventor: Daniel Hawkins, Fremont, CA (US)

(73) Assignee: SHOCKWAVE MEDICAL, INC., Santa Clara, CA (US)

( * ) Notice: Subject to any disclaimer, the term of this patent is extended or adjusted under 35 U.S.C. 154(b) by 377 days.

(21) Appl. No.: 15/937,720

(22) Filed: Mar. 27, 2018

Related U.S. Application Data

(60) Provisional application No. 62/489,951, filed on Apr. 25, 2017.

(51) Int. Cl.
| | |
|---|---|
| *A61B 17/22* | (2006.01) |
| *A61M 25/10* | (2013.01) |
| *A61M 25/00* | (2006.01) |

(52) U.S. Cl.
CPC ..... *A61B 17/22022* (2013.01); *A61M 25/104* (2013.01); *A61B 2017/22001* (2013.01);
(Continued)

(58) Field of Classification Search
CPC .... A61B 17/22022; A61B 2017/22001; A61B 2017/22025; A61B 2017/22038; A61B 2017/22061; A61B 2017/22062; A61B 2017/22065; A61B 17/2202; A61B 2017/22051; A61B 2017/22021; A61B 2017/22024; A61B 17/22012; A61B 17/22029; A61B 17/225; A61B 17/2251; A61B 18/1492; A61B 2017/22098;
(Continued)

(56) References Cited

U.S. PATENT DOCUMENTS

| | | |
|---|---|---|
| 3,413,976 A | 12/1968 | Roze |
| 3,785,382 A | 1/1974 | Schmidt-Kloiber et al. |
| | (Continued) | |

FOREIGN PATENT DOCUMENTS

| | | |
|---|---|---|
| CN | 1269708 A | 10/2000 |
| CN | 102057422 A | 5/2011 |
| | (Continued) | |

OTHER PUBLICATIONS

Advisory Action received for U.S. Appl. No. 12/482,995, dated Jun. 2, 2014, 3 pages.

(Continued)

*Primary Examiner* — Eric J Rosen
*Assistant Examiner* — Mikail A Mannan
(74) *Attorney, Agent, or Firm* — Morrison & Foerster LLP

(57) ABSTRACT

Described herein are shock wave devices and methods for the treatment of vascular plaques. One variation of a shock wave device may include a pair of elongated, flexible concentric tubes comprising an inner tube and an outer tube. The inner tube and the outer tube may be connected together at one end, and at least a portion of the volume between the inner tube and the outer tube may be filled with a conductive fluid via the other end. At least two electrodes may be positioned between the inner tube and the outer tube, the at least two electrodes being electrically connectable to a voltage source and configured to generate shock waves in the conductive fluid in response to voltage pulses.

11 Claims, 22 Drawing Sheets

(52) U.S. Cl.
CPC ............ *A61B 2017/22025* (2013.01); *A61B 2017/22038* (2013.01); *A61B 2017/22061* (2013.01); *A61B 2017/22062* (2013.01); *A61B 2017/22065* (2013.01); *A61M 2025/0004* (2013.01)

(58) Field of Classification Search
CPC .... A61B 17/22004; A61B 2017/22028; A61B 2017/22058; A61B 2017/00084; A61B 2017/00038; A61B 2017/00154; A61B 2018/0022; A61B 18/245; A61B 2018/00214; A61B 2018/1213; A61B 18/26; A61B 2017/00243; A61B 2017/22015; A61B 2017/22067; A61B 2018/00422; A61B 2018/00547; A61B 18/18; A61B 2017/22084; A61B 2018/00577; A61B 2018/00642; A61B 2018/00666; A61B 2018/00821; A61B 2018/00892; A61B 2018/1467; A61M 25/104; A61M 2025/0004

See application file for complete search history.

(56) References Cited

U.S. PATENT DOCUMENTS

| | | |
|---|---|---|
| 3,902,499 A | 9/1975 | Shene |
| 4,027,674 A | 6/1977 | Tessler et al. |
| 4,662,126 A | 5/1987 | Malcolm |
| 4,671,254 A | 6/1987 | Fair |
| 4,685,458 A | 8/1987 | Leckrone |
| 4,809,682 A | 3/1989 | Forssmann et al. |
| 4,900,303 A | 2/1990 | Lemelson |
| 5,009,232 A | 4/1991 | Hassler et al. |
| 5,057,103 A | 10/1991 | Davis |
| 5,057,106 A | 10/1991 | Kasevich et al. |
| 5,078,717 A | 1/1992 | Parins et al. |
| 5,103,804 A | 4/1992 | Abele et al. |
| 5,152,767 A | 10/1992 | Sypal et al. |
| 5,152,768 A | 10/1992 | Bhatta |
| 5,176,675 A | 1/1993 | Watson et al. |
| 5,245,988 A | 9/1993 | Einars et al. |
| 5,246,447 A | 9/1993 | Rosen et al. |
| 5,281,231 A | 1/1994 | Rosen et al. |
| 5,321,715 A | 6/1994 | Trost |
| 5,324,255 A | 6/1994 | Passafaro et al. |
| 5,336,234 A | 8/1994 | Vigil et al. |
| 5,362,309 A | 11/1994 | Carter |
| 5,364,393 A | 11/1994 | Auth et al. |
| 5,368,591 A | 11/1994 | Lennox et al. |
| 5,395,335 A | 3/1995 | Jang |
| 5,417,208 A | 5/1995 | Winkler |
| 5,425,735 A | 6/1995 | Rosen et al. |
| 5,472,406 A | 12/1995 | de la Torre et al. |
| 5,582,578 A | 12/1996 | Zhong et al. |
| 5,603,731 A | 2/1997 | Whitney |
| 5,609,606 A | 3/1997 | O'Boyle |
| 5,662,590 A | 9/1997 | de la Torre et al. |
| 5,931,805 A | 8/1999 | Brisken |
| 6,007,530 A | 12/1999 | Doernhoefer et al. |
| 6,033,371 A | 3/2000 | Torre et al. |
| 6,083,232 A | 7/2000 | Cox |
| 6,186,963 B1 | 2/2001 | Schwarze et al. |
| 6,210,408 B1 | 4/2001 | Chandrasekaran et al. |
| 6,217,531 B1 | 4/2001 | Reitmajer |
| 6,277,138 B1 | 8/2001 | Levinson et al. |
| 6,287,272 B1 | 9/2001 | Brisken et al. |
| 6,352,535 B1 | 3/2002 | Lewis et al. |
| 6,367,203 B1 | 4/2002 | Graham et al. |
| 6,371,971 B1 | 4/2002 | Tsugita et al. |
| 6,398,792 B1 | 6/2002 | O'Connor |
| 6,406,486 B1 | 6/2002 | de la Torre et al. |
| 6,514,203 B2 | 2/2003 | Bukshpan |
| 6,524,251 B2 | 2/2003 | Rabiner et al. |
| 6,589,253 B1 | 7/2003 | Cornish et al. |
| 6,607,003 B1 | 8/2003 | Wilson |
| 6,638,246 B1 | 10/2003 | Naimark et al. |
| 6,652,547 B2 | 11/2003 | Rabiner et al. |
| 6,736,784 B1 | 5/2004 | Menne et al. |
| 6,740,081 B2 | 5/2004 | Hilal |
| 6,755,821 B1 | 6/2004 | Fry |
| 6,989,009 B2 | 1/2006 | Lafontaine |
| 7,241,295 B2 | 7/2007 | Maguire |
| 7,505,812 B1 | 3/2009 | Eggers et al. |
| 7,569,032 B2 | 8/2009 | Naimark et al. |
| 7,873,404 B1 | 1/2011 | Patton |
| 8,556,813 B2 | 10/2013 | Cioanta et al. |
| 8,728,091 B2 | 5/2014 | Hakala et al. |
| 8,747,416 B2 | 6/2014 | Hakala et al. |
| 8,888,788 B2 | 11/2014 | Hakala et al. |
| 8,956,371 B2 | 2/2015 | Hawkins et al. |
| 9,005,216 B2 | 4/2015 | Hakala et al. |
| 9,011,463 B2 | 4/2015 | Adams et al. |
| 9,333,000 B2 | 5/2016 | Hakala et al. |
| 9,433,428 B2 | 9/2016 | Hakala et al. |
| 9,642,673 B2 | 5/2017 | Adams et al. |
| 9,743,984 B1 * | 8/2017 | Curley .................. A61B 18/04 |
| 9,993,292 B2 | 6/2018 | Adams et al. |
| 9,999,788 B2 | 6/2018 | Gattiker et al. |
| 2001/0044596 A1 | 11/2001 | Jaafar |
| 2002/0045890 A1 | 4/2002 | Brisken et al. |
| 2002/0177889 A1 | 11/2002 | Brisken et al. |
| 2003/0004434 A1 | 1/2003 | Greco et al. |
| 2003/0176873 A1 | 9/2003 | Chernenko et al. |
| 2003/0229370 A1 | 12/2003 | Miller |
| 2004/0006333 A1 | 1/2004 | Arnold et al. |
| 2004/0010249 A1 | 1/2004 | Truckai et al. |
| 2004/0044308 A1 | 3/2004 | Naimark et al. |
| 2004/0097963 A1 | 5/2004 | Seddon |
| 2004/0097996 A1 | 5/2004 | Rabiner et al. |
| 2004/0162508 A1 | 8/2004 | Uebelacker |
| 2004/0254570 A1 | 12/2004 | Hadjicostis et al. |
| 2005/0015953 A1 | 1/2005 | Keidar |
| 2005/0021013 A1 | 1/2005 | Visuri et al. |
| 2005/0113722 A1 | 5/2005 | Schultheiss |
| 2005/0113822 A1 | 5/2005 | Fuimaono et al. |
| 2005/0228372 A1 | 10/2005 | Truckai et al. |
| 2005/0251131 A1 | 11/2005 | Lesh |
| 2006/0004286 A1 | 1/2006 | Chang et al. |
| 2006/0069424 A1 | 3/2006 | Acosta et al. |
| 2006/0184076 A1 | 8/2006 | Gill et al. |
| 2006/0190022 A1 | 8/2006 | Beyar et al. |
| 2007/0016112 A1 | 1/2007 | Schultheiss et al. |
| 2007/0088380 A1 | 4/2007 | Hirszowicz et al. |
| 2007/0239082 A1 | 10/2007 | Schultheiss et al. |
| 2007/0239253 A1 | 10/2007 | Jagger et al. |
| 2007/0244423 A1 | 10/2007 | Zumeris et al. |
| 2007/0255270 A1 | 11/2007 | Carney |
| 2007/0282301 A1 | 12/2007 | Segalescu et al. |
| 2008/0097251 A1 | 4/2008 | Babaev |
| 2008/0188913 A1 | 8/2008 | Stone et al. |
| 2009/0041833 A1 | 2/2009 | Bettinger et al. |
| 2009/0247945 A1 | 10/2009 | Levit et al. |
| 2009/0254114 A1 | 10/2009 | Hirszowicz et al. |
| 2009/0312768 A1 | 12/2009 | Hawkins et al. |
| 2010/0016862 A1 | 1/2010 | Hawkins et al. |
| 2010/0036294 A1 | 2/2010 | Mantell et al. |
| 2010/0114020 A1 | 5/2010 | Hawkins et al. |
| 2010/0114065 A1 | 5/2010 | Hawkins et al. |
| 2010/0121322 A1 | 5/2010 | Swanson |
| 2010/0305565 A1 | 12/2010 | Truckai et al. |
| 2011/0034832 A1 | 2/2011 | Cioanta et al. |
| 2011/0118634 A1 | 5/2011 | Golan |
| 2011/0166570 A1 | 7/2011 | Hawkins et al. |
| 2011/0208185 A1 | 8/2011 | Diamant et al. |
| 2011/0257523 A1 | 10/2011 | Hastings et al. |
| 2011/0295227 A1 | 12/2011 | Hawkins et al. |
| 2012/0071889 A1 | 3/2012 | Mantell et al. |
| 2012/0095461 A1 | 4/2012 | Herscher et al. |
| 2012/0116289 A1 | 5/2012 | Hawkins et al. |
| 2012/0203255 A1 | 8/2012 | Hawkins et al. |
| 2012/0221013 A1 | 8/2012 | Hawkins et al. |
| 2013/0030431 A1 | 1/2013 | Adams |

(56) References Cited

U.S. PATENT DOCUMENTS

| | | | |
|---|---|---|---|
| 2013/0030447 A1 | 1/2013 | Adams | |
| 2013/0116714 A1 | 5/2013 | Adams et al. | |
| 2013/0150874 A1 | 6/2013 | Kassab | |
| 2014/0005576 A1 | 1/2014 | Adams et al. | |
| 2014/0039513 A1* | 2/2014 | Hakala | A61B 17/2202 606/128 |
| 2014/0046229 A1 | 2/2014 | Hawkins et al. | |
| 2014/0052145 A1 | 2/2014 | Adams et al. | |
| 2014/0052147 A1 | 2/2014 | Hakala et al. | |
| 2014/0074111 A1 | 3/2014 | Hakala et al. | |
| 2014/0074113 A1 | 3/2014 | Hakala et al. | |
| 2014/0214061 A1 | 7/2014 | Adams et al. | |
| 2014/0243847 A1 | 8/2014 | Hakala et al. | |
| 2014/0288570 A1 | 9/2014 | Adams | |
| 2015/0045675 A1* | 2/2015 | Chernomorsky | A61B 1/00094 600/471 |
| 2015/0073430 A1 | 3/2015 | Hakala et al. | |
| 2015/0238208 A1 | 8/2015 | Adams et al. | |
| 2015/0320432 A1 | 11/2015 | Adams et al. | |
| 2016/0183957 A1 | 6/2016 | Hakala et al. | |
| 2016/0324534 A1 | 11/2016 | Hawkins et al. | |
| 2016/0331389 A1 | 11/2016 | Hakala et al. | |
| 2017/0135709 A1 | 5/2017 | Nguyen et al. | |

FOREIGN PATENT DOCUMENTS

| | | |
|---|---|---|
| CN | 102271748 A | 12/2011 |
| CN | 102355856 A | 2/2012 |
| CN | 102765785 A | 11/2012 |
| DE | 3038445 A1 | 5/1982 |
| DE | 202006014285 U1 | 12/2006 |
| EP | 0442199 A2 | 8/1991 |
| EP | 0571306 A1 | 11/1993 |
| EP | 0647435 A1 | 4/1995 |
| JP | 62-275446 A | 11/1987 |
| JP | 6-125915 A | 5/1994 |
| JP | 7-47135 A | 2/1995 |
| JP | 10-99444 A | 4/1998 |
| JP | 10-513379 A | 12/1998 |
| JP | 2002-538932 A | 11/2002 |
| JP | 2004-81374 A | 3/2004 |
| JP | 2005-501597 A | 1/2005 |
| JP | 2005-95410 A | 4/2005 |
| JP | 2005-515825 A | 6/2005 |
| JP | 2006-516465 A | 7/2006 |
| JP | 2007-532182 A | 11/2007 |
| JP | 2011-524203 A | 9/2011 |
| JP | 2012-508042 A | 4/2012 |
| WO | 1996/024297 A1 | 8/1996 |
| WO | 1999/000060 A1 | 1/1999 |
| WO | 1999/02096 A1 | 1/1999 |
| WO | 2000/056237 A2 | 9/2000 |
| WO | 2004/069072 A2 | 8/2004 |
| WO | 2005/099594 A1 | 10/2005 |
| WO | 2006/127158 A2 | 11/2006 |
| WO | 2007/149905 A2 | 12/2007 |
| WO | 2009/121017 A1 | 10/2009 |
| WO | 2009/152352 A2 | 12/2009 |
| WO | 2010/014515 A2 | 2/2010 |
| WO | 2011/094111 A2 | 8/2011 |
| WO | 2011/143468 A2 | 11/2011 |
| WO | 2012/025833 A2 | 3/2012 |
| WO | 2013/059735 A1 | 4/2013 |
| WO | 2015/017499 A1 | 2/2015 |

OTHER PUBLICATIONS

Advisory Action received for U.S. Appl. No. 12/482,995, dated Sep. 29, 2011, 2 pages.
Advisory Action received for U.S. Appl. No. 2/581,295, dated Jul. 3, 2014, 3 pages.
Advisory Action received for U.S. Appl. No. 13/049,199, dated Jun. 7, 2012, 3 pages.
Advisory Action received for U.S. Appl. No. 13/267,383, dated Jan. 6, 2014, 4 pages.
Advisory Action received for U.S. Appl. No. 13/615,107, dated Nov. 6, 2015, 3 pages.
Cleveland et al., "The Physics of Shock Wave Lithotripsy", Extracorporeal Shock Wave Lithotripsy, Part IV, Chapter 38, 2012, pp. 317-332.
Connors et al., "Renal Nerves Mediate Changes in Contralateral Renal Blood Flow after Extracorporeal Shockwave Lithotripsy", Nephron Physiology, vol. 95, 2003, pp. 67-75.
Decision to Grant received for European Patent Application No. 13756766.5, dated May 27, 2016, 2 pages.
Decision to Grant received for Japanese Patent Application No. 2011-513694, dated Oct. 7, 2014, 3 pages (Official Copy Only) (See Communication under 37 CFR § 1.98(a) (3)).
Extended European Search Report (includes Supplementary European Search Report and Search Opinion) received for European Patent Application No. 09763640.1, dated Oct. 10, 2013, 5 pages.
Extended European Search Report received for European Patent Application No. 13827971.6, dated Apr. 12, 2016, 8 pages.
Final Office Action received for U.S. Appl. No. 12/482,995, dated Feb. 20, 2014, 11 pages.
Final Office Action received for U.S. Appl. No. 12/581,295, dated Jun. 5, 2014, 14 pages.
Final Office Action received for U.S. Appl. No. 13/049,199 dated Aug. 11, 2014, 8 pages.
Final Office Action received for U.S. Appl. No. 13/267,383, dated May 28, 2015, 12 pages.
Final Office Action received for U.S. Appl. No. 13/267,383, dated Oct. 25, 2013, 8 pages.
Final Office Action received for U.S. Appl. No. 13/534,658, dated Aug. 23, 2016, 11 pages.
Final Office Action received for U.S. Appl. No. 13/615,107, dated Sep. 1, 2015, 9 pages.
Final Office Action received for U.S. Appl. No. 13/646,570, dated Dec. 23, 2014, 10 pages.
Final Office Action received for U.S. Appl. No. 14/271,342, dated Feb. 27, 2015, 7 pages.
Gambihler et al., "Permeabilization of the Plasma Membrane of L1210 Mouse Leukemia Cells Using Lithotripter Shock Waves", The Journal of Membrane Biology, vol. 141, 1994, pp. 267-275.
Grassi et al., "Novel Antihypertensive Therapies: Renal Sympathetic Nerve Ablation and Carotid Baroreceptor Stimulation", Current Hypertension Reports, vol. 14, 2012, pp. 567-572.
Intention to Grant received for European Patent Application No. 13756766.5, dated Jan. 8, 2016, 5 pages.
International Preliminary Report on Patentability received for PCT Patent Application No. PCT/US2009/047070, dated Dec. 23, 2010, 7 pages.
International Preliminary Report on Patentability received for PCT Patent Application No. PCT/US2011/047070, dated Feb. 21, 2013, 7 pages.
International Preliminary Report on Patentability received for PCT Patent Application No. PCT/US2012/023172, dated Aug. 15, 2013, 6 pages.
International Preliminary Report on Patentability received for PCT Patent Application No. PCT/US2013/031805, dated Feb. 19, 2015, 11 pages.
International Preliminary Report on Patentability received for PCT Patent Application No. PCT/US2013/039987, dated Nov. 20, 2014, 11 pages.
International Preliminary Report on Patentability received for PCT Patent Application No. PCT/US2013/048277, dated Jan. 8, 2015, 9 pages.
International Preliminary Report on Patentability received for PCT Patent Application No. PCT/US2013/055431, dated Feb. 26, 2015, 7 pages.
International Preliminary Report on Patentability received for PCT Patent Application No. PCT/US2013/059533, dated Mar. 26, 2015, 10 pages.
International Preliminary Report on Patentability received for PCT Patent Application No. PCT/US2012/063925, dated May 22, 2014, 12 pages.

(56) References Cited

OTHER PUBLICATIONS

International Search Report and Written Opinion received for PCT Patent Application No. PCT/US2013/031805, dated May 20, 2013, 13 pages.
International Search Report and Written Opinion received for PCT Patent Application No. PCT/US2016/060817, dated Feb. 20, 2017, 13 pages.
International Search Report and Written Opinion received for PCT Patent Application No. PCT/US2013/039987, dated Sep. 23, 2013, 15 pages.
International Search Report and Written Opinion received for PCT Patent Application No. PCT/US2013/048277, dated Oct. 2, 2013, 14 pages.
International Search Report and Written Opinion received for PCT Patent Application No. PCT/US2013/055431, dated Nov. 12, 2013, 9 pages.
International Search Report and Written Opinion received for PCT Patent Application No. PCT/US2013/059533, dated Nov. 7, 2013, 14 pages.
International Search Report and Written Opinion received for PCT Patent Application No. PCT/US2015/029088, dated Jul. 16, 2015, 13 pages.
International Search Report received for PCT Patent Application No. PCT/US2009/047070, dated Jan. 19, 2010, 4 pages.
International Search Report received for PCT Patent Application No. PCT/US2012/023172, dated Sep. 28, 2012, 3 pages.
International Written Opinion received for PCT Patent Application No. PCT/US2009/047070, dated Jan. 19, 2010, 5 pages.
International Written Opinion received for PCT Patent Application No. PCT/US2011/047070, dated May 1, 2012, 5 pages.
International Written Opinion received for PCT Patent Application No. PCT/US2012/023172, dated Sep. 28, 2012, 4 pages.
Kodama et al., "Shock Wave-Mediated Molecular Delivery into Cells", Biochimica et Biophysica Acta., vol. 1542, 2002, pp. 186-194.
Lauer et al., "Shock Wave Permeabilization as a New Gene Transfer Method", Gene Therapy, vol. 4, 1997, pp. 710-715.
Non-Final Office Action received for U.S. Appl. No. 12/482,995, dated Aug. 13, 2014, 10 pages.
Non-Final Office Action received for U.S. Appl. No. 12/482,995, dated Jul. 12, 2013, 11 pages.
Non-Final Office Action received for U.S. Appl. No. 13/465,264, dated Oct. 29, 2014, 13 pages.
Non-Final Office Action received for U.S. Appl. No. 13/534,658, dated Mar. 11, 2016, 12 pages.
Non-Final Office Action received for U.S. Appl. No. 13/646,570, dated Oct. 29, 2014, 10 pages.
Non-Final Office Action received for U.S. Appl. No. 14/079,463, dated Mar. 4, 2014, 9 pages.
Non-Final Office Action received for U.S. Appl. No. 14/218,858, dated Mar. 30, 2016, 13 pages.
Non-Final Office Action received for U.S. Appl. No. 14/515,130, dated Jan. 14, 2016, 16 pages.
Non-Final Office Action received for U.S. Appl. No. 12/501,619, dated Jan. 28, 2014, 10 pages.
Non-Final Office Action received for U.S. Appl. No. 12/581,295, dated Jan. 15, 2015, 14 pages.
Non-Final Office Action received for U.S. Appl. No. 12/581,295, dated Mar. 10, 2014, 11 pages.
Non-Final Office Action received for U.S. Appl. No. 13/049,199, dated Feb. 4, 2014, 8 pages.
Non-Final Office Action received for U.S. Appl. No. 13/267,383, dated Feb. 25, 2015, 9 pages.
Non-Final Office Action received for U.S. Appl. No. 13/465,264, dated Dec. 23, 2014, 13 pages.
Non-Final Office Action received for U.S. Appl. No. 13/615,107, dated Apr. 24, 2015, 9 pages.
Non-Final Office Action received for U.S. Appl. No. 13/646,583, dated Oct. 31, 2014, 8 pages.
Non-Final Office Action received for U.S. Appl. No. 14/061,554, dated Mar. 12, 2014, 14 pages.
Non-Final Office Action received for U.S. Appl. No. 14/271,276, dated Aug. 4, 2014, 7 pages.
Non-Final Office Action received for U.S. Appl. No. 14/271,342, dated Sep. 2, 2014, 6 pages.
Non-Final Office Action received for U.S. Appl. No. 15/474,885, dated Oct. 5, 2017, 9 pages.
Non-Final Office Action received for U.S. Appl. No. 14/273,063, dated Jun. 3, 2016, 9 pages.
Non-Final Office Action received for U.S. Appl. No. 12/611,997, dated Nov. 26, 2014, 8 pages.
Notice of Acceptance received for Australian Patent Application No. 2009257368, dated Aug. 28, 2014, 2 pages.
Notice of Allowance received for Japanese Patent Application No. 2015-520522, dated Feb. 23, 2017, 3 pages (Official Copy Only) (See Communication under 37 CFR § 1.98(a) (3)).
Notice of Allowance received for Chinese Patent Application No. 201380033808.3, dated Dec. 29, 2016, 4 pages (Official Copy Only) (See Communication under 37 CFR § 1.98(a) (3)).
Notice of Allowance received for Chinese Patent Application No. 201380041656.1, dated Mar. 3, 2017, 4 pages (Official Copy Only) (See Communication under 37 CFR § 1.98(a) (3)).
Notice of Allowance received for U.S. Appl. No. 14/515,130, dated May 2, 2016, 8 pages.
Notice of Allowance received for Canadian Patent Application No. 2,727,429, dated May 26, 2015, 1 page.
Notice of Allowance received for U.S. Appl. No. 15/474,885, dated Feb. 14, 2018, 5 pages.
Notice of Allowance received for U.S. Appl. No. 12/482,995, dated Dec. 24, 2014, 6 pages.
Notice of Allowance received for U.S. Appl. No. 12/581,295, dated Jul. 10, 2015, 15 pages.
Notice of Allowance received for U.S. Appl. No. 12/581,295, dated Jul. 29, 2015, 7 pages.
Notice of Allowance received for U.S. Appl. No. 13/049,199, dated Dec. 15, 2014, 7 pages.
Notice of Allowance received for U.S. Appl. No. 13/049,199, dated Jan. 13, 2015, 4 pages.
Notice of Allowance received for U.S. Appl. No. 13/465,264, dated May 8, 2015, 7 pages.
Notice of Allowance received for U.S. Appl. No. 13/534,658, dated Jan. 5, 2017, 6 pages.
Notice of Allowance received for U.S. Appl. No. 13/534,658, dated Jan. 18, 2017, 4 pages.
Notice of Allowance received for U.S. Appl. No. 13/615,107, dated Dec. 31, 2015, 10 pages.
Notice of Allowance received for U.S. Appl. No. 13/646,570, dated Mar. 11, 2015, 7 pages.
Notice of Allowance received for U.S. Appl. No. 13/777,807, dated May 19, 2015, 13 pages.
Notice of Allowance received for U.S. Appl. No. 13/831,543, dated Oct. 8, 2014, 14 pages.
Notice of Allowance received for U.S. Appl. No. 13/957,276, dated Aug. 28, 2015, 9 pages.
Notice of Allowance received for U.S. Appl. No. 14/061,554, dated Apr. 25, 2014, 8 pages.
Notice of Allowance received for U.S. Appl. No. 14/079,463, dated Apr. 1, 2014, 5 pages.
Notice of Allowance received for U.S. Appl. No. 14/218,858, dated Aug. 26, 2016, 8 pages.
Notice of Allowance received for U.S. Appl. No. 14/271,276, dated Feb. 25, 2015, 8 pages.
Notice of Allowance received for U.S. Appl. No. 14/271,342, dated Mar. 13, 2015, 5 pages.
Notice of Allowance received for U.S. Appl. No. 14/515,130, dated May 25, 2016, 3 pages.
Office Action received for Australian Patent Application No. 2013284490, dated Jun. 5, 2017, 4 pages.
Office Action received for Australian Patent Application No. 2013300176, dated Nov. 10, 2016, 2 pages.
Office Action received for Australian Patent Application No. 2009257368, dated Apr. 28, 2014, 4 pages.

(56) References Cited

OTHER PUBLICATIONS

Office Action received for Australian Patent Application No. 2009257368, dated Jul. 31, 2013, 4 pages.
Office Action received for Canadian Patent Application No. 2,727,429, dated Apr. 14, 2015, 4 pages.
Office Action received for Chinese Patent Application No. 201380033808.3, dated Jul. 5, 2016, 9 pages (3 pages of English Translation and 6 pages of Official Copy).
Office Action received for Chinese Patent Application No. 201380041656.1, dated Jul. 5, 2016, 9 pages (4 pages of English Translation and 5 pages of Official Copy).
Office Action received for Chinese Patent Application No. 201380042887.4, dated Aug. 8, 2016, 9 pages (4 pages of English Translation and 5 pages of Official Copy).
Office Action received for Japanese Patent Application No. 2015-526523, dated Jan. 25, 2017, 8 pages (5 pages of English Translation and 3 pages of Official Copy).
Office Action received for Japanese Patent Application No. 2011-513694, dated Aug. 27, 2013, 6 pages (2 pages of English Translation and 6 pages of Official Copy).
Office Action received for Japanese Patent Application No. 2011-513694, dated Jun. 10, 2014, 4 pages (2 pages of English Translation and 2 pages of Official Copy).
Office Action received for Japanese Patent Application No. 2014-158517, dated May 19, 2015, 5 pages (2 pages of English Translation and 3 pages of Official Copy).
Office Action Received for Japanese Patent Application No. 2011-534914, dated Jul. 15, 2014, 3 pages (1 page of English Translation and 2 pages of Official Copy).
Rosenschein et al., "Shock-Wave Thrombus Ablation, a New Method for Noninvasive Mechanical Thrombolysis", The American Journal of Cardiology, vol. 70, Nov. 15, 1992, pp. 1358-1361.
Zhong et al., "Transient Oscillation of Cavitation Bubbles Near Stone Surface During Electrohydraulic Lithotripsy", Journal of Endourology, vol. 11, No. 1, Feb. 1997, pp. 55-61.

\* cited by examiner

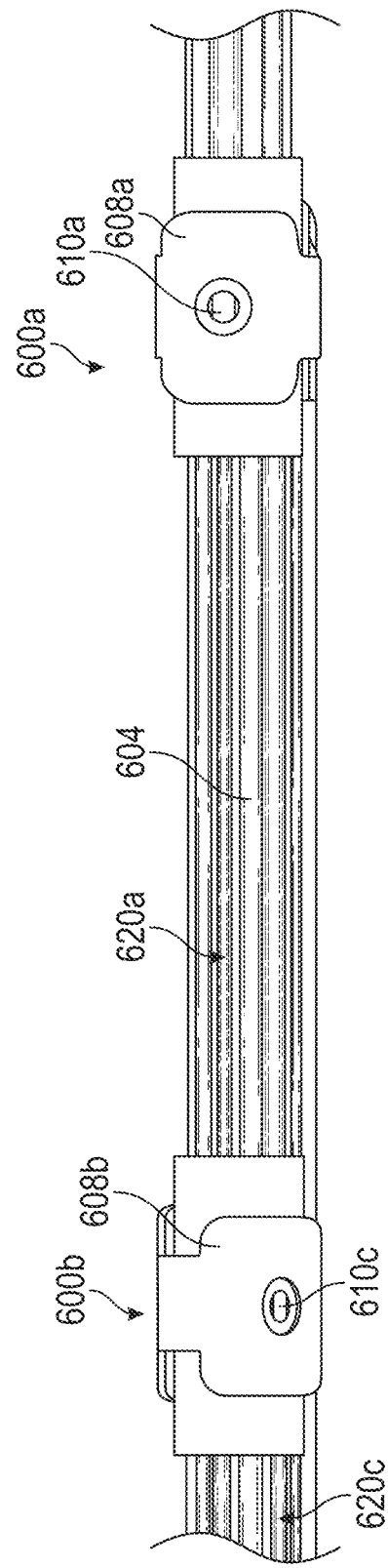
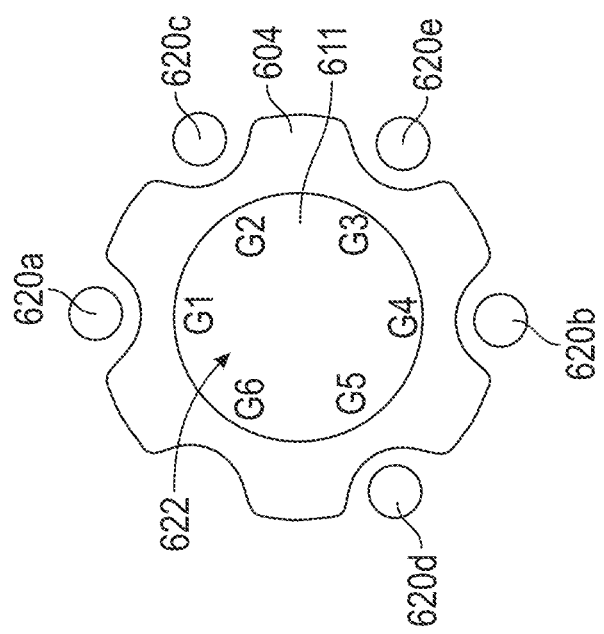
FIG. 6A
FIG. 6B

SHOCK WAVE DEVICE FOR TREATING VASCULAR PLAQUES

PRIORITY

This application claims prior to U.S. Provisional Application Ser. No. 62/489,951, filed Apr. 25, 2017, the entire disclosure of which is incorporated by reference.

FIELD

The present disclosure relates generally to shock wave electrodes, and, more specifically, to electrodes for the generation of shock waves within vascular structures.

BACKGROUND

The subject invention relates to treating calcified lesions in blood vessels. One common approach to addressing this issue is balloon angioplasty. In this type of procedure, a catheter, carrying a balloon, is advanced into the vasculature along a guide wire until the balloon is aligned with the occlusion. The balloon is then pressurized in a manner to reduce or break the occlusion.

More recently, the assignee herein has developed a treatment system that includes electrodes within an angioplasty type balloon. In use, the balloon is advanced into the region of the occlusion. The balloon is then partially pressurized with a conductive fluid. A series of high voltage pulses are applied to the electrodes, with each pulse generating a shockwave in the conductive fluid. The shock waves pass through the balloon wall and into the occlusion, cracking the calcium deposits. Once the calcium deposit has been cracked, the balloon can be further expanded to open the vessel. The latter system is disclosed in U.S. Pat. Nos. 8,956,371 and 8,888,788, both of which are incorporated herein by reference.

More recently, the assignee herein has proposed providing an electrode on the tip of a guide wire for generating forward directed shock waves. This approach is disclosed in U.S. Patent Publication No. 2015/0320432, also incorporated herein by reference.

The subject invention relates to yet another alternative for placing shock wave electrodes near an occlusion. This approach can be used alone or in conjunction with an angioplasty balloon.

BRIEF SUMMARY

Described herein are shock wave devices and methods for the treatment of vascular plaques. One example of a shock wave device may include a pair of elongated, flexible concentric tubes comprising an inner tube and an outer tube, wherein: the pair of concentric tubes have a fluid input end and a treatment end, the fluid input end is located near a proximal end of the pair of concentric tubes, the treatment end is located near a distal end of the pair of concentric tubes, the inner tube and the outer tube are connected together at the treatment end, and at least a portion of the volume between the inner tube and the outer tube is finable with a conductive fluid via the fluid input end; and at least two electrodes positioned between the inner tube and the outer tube, the at least two electrodes being electrically connectable to a voltage source and configured to generate shock waves in the conductive fluid in response to voltage pulses. The pair of concentric tubes may be carried by a guide wire. A fluid source and a fluid pump may be configured to deliver fluid from the fluid source to the fluid input end of the pair of concentric tubes.

In some variations, the shock wave device further includes a treatment appliance located within the inner tube and configured to be advanced out of the inner tube. The treatment appliance may be an angioplasty balloon.

In one variation, the at least two electrodes include a first inner electrode disposed at a first location adjacent to an outer surface of the inner tube and an outer electrode circumferentially disposed around the inner tube, the outer electrode having a first aperture aligned with the first inner electrode, wherein the first inner electrode and the outer electrode are separated by an insulating sheath, the insulating sheath having a second aperture coaxially aligned with the first aperture in the outer electrode so that when a voltage is applied across the electrodes, a first shock wave will be initiated from the first location. The size of the first aperture in the outer electrode may be larger than the size of the second aperture in the insulating sheath. A first wire may be connected to the first inner electrode and a second wire may be connected to the outer electrode, and the inner tube may have first and second grooves that extend along the length of the inner tube, and the first wire may be slidably disposed within the first groove and the second wire may be slidably disposed within the second groove.

In some variations, the shock wave device further includes a second inner electrode disposed at a second location adjacent to the outer surface of the inner tube and circumferentially offset from the first location of the first inner electrode, wherein the outer electrode sheath has a third aperture aligned with the second inner electrode, and the insulating sheath has a fourth aperture coaxially aligned with the third aperture in the outer electrode so that when a voltage is applied across the electrodes, first and second shock waves will be initiated from two circumferentially offset locations. A first wire may be connected to the first inner electrode, a second wire may be connected to the second inner electrode, and a third wire may be connected to the outer electrode, and the inner tube may have first, second, and third grooves that extend along the length of the inner tube, and the first wire may be slidably disposed within the first groove, the second wire may be slidably disposed within the second groove, and the third wire may be slidably disposed within the third groove. The second location of the second inner electrode may be circumferentially offset 90 degrees from the first location of the first inner electrode. Alternatively, the second location of the second inner electrode may be circumferentially opposite from the first location of the first inner electrode.

In another variation, the at least two electrodes may include a first electrode circumferentially disposed around the inner tube, the first electrode including a first recess along an edge of the first electrode and a second electrode circumferentially disposed around the inner tube and adjacent to the first electrode, the second electrode including a first projection along an edge of the second electrode that is received by the first recess of the first electrode, wherein a first spark gap is formed by a separation between the first projection and the first recess, and wherein when a voltage is applied across the electrodes, a current flows across the first spark gap between the first electrode and the second electrode such that a shock wave is initiated at the first spark gap. The first recess may have a concave curve and the first protrusion may have a convex curve that corresponds with the concave curve. Each of the first and second electrodes may include a proximal end, a distal end, and a spiral body therebetween. The spiral body may include one or more helices that wrap around the outer surface of the inner tube.

In some variations, the shock wave device further includes a third electrode circumferentially disposed around the inner tube and adjacent to the second electrode, wherein the second electrode further includes a second recess and the third electrode includes a second projection that is received by the second recess of the second electrode, and wherein a space between the second projection of the third electrode and the second recess of the second electrode forms a second spark gap, wherein when a voltage is applied across the first and third electrodes, a current flows across the first spark gap to initiate a first shock wave and across the second spark gap to initiate a second shock wave.

One variation of a method for delivering shock waves to treat vascular plaques includes introducing a shock wave device into a patient's vasculature; advancing the shock wave device within the vasculature such that the shock wave device is aligned with a first treatment region; and activating a voltage source to apply shock waves to the first treatment region with at least two electrodes. The shock wave device may then be advanced further within the vasculature such that the shock wave device is aligned with a second treatment region, and the voltage source may be activated to apply shock waves to the second treatment region. In some examples, the method further includes withdrawing the shock wave device from the patient's vasculature, introducing an angioplasty balloon into the patient's vasculature; advancing the angioplasty balloon to the first or second treatment region; and inflating the angioplasty balloon in the first or second treatment region to increase the diameter of the vasculature in the first or second treatment region.

Another variation of a method for delivering shock waves to treat vascular plaques includes introducing a shock wave device into a patient's vasculature; advancing the shock wave device within the vasculature such that the shock wave device is aligned with a first treatment region; activating the voltage source to apply shock waves to the first treatment region with the at least two electrodes; retracting the shock wave device from the first treatment region; advancing an angioplasty balloon out of the inner tube and into the first treatment region; inflating the angioplasty balloon in the first treatment region to increase the diameter of the vasculature in the first treatment region; and deflating the angioplasty balloon. In some examples, the method further includes advancing the shock wave device further within the vasculature such that the shock wave device is aligned with a second treatment region; activating the voltage source to apply shock waves to the second treatment region with the at least two electrodes; retracting the shock wave device from the second treatment region; advancing the angioplasty balloon out of the inner tube and into the second treatment region; inflating the angioplasty balloon in the second treatment region to increase the diameter of the vasculature in the second treatment region; and deflating the angioplasty balloon.

Another variation of a method for delivering shock waves to treat vascular plaques includes introducing an angioplasty balloon into a patient's vasculature; introducing a shock wave device into the patient's vasculature; advancing the angioplasty balloon into a first treatment region; inflating the angioplasty balloon to increase the diameter of the vasculature in the first treatment region; deflating the angioplasty balloon; advancing the shock wave device toward the angioplasty balloon until the angioplasty balloon is received within the inner tube of the shock wave device and the shock wave device is aligned with the first treatment region; and activating the voltage source to apply shock waves to the first treatment region with the at least two electrodes. In some examples, the method further includes advancing the angioplasty balloon out of the inner tube and into a second treatment region; inflating the angioplasty balloon to increase the diameter of the vasculature in the second treatment region; deflating the angioplasty balloon; advancing the shock wave device toward the angioplasty balloon until the angioplasty balloon is received within the inner tube and the shock wave device is aligned with the second Treatment region; and activating the voltage source to apply shock waves to the second treatment region with the at least two electrodes. In other examples, the method further includes advancing the shock wave device and the angioplasty balloon toward a second treatment region; advancing the angioplasty balloon out of the inner tube and into the second treatment region; inflating the angioplasty balloon to increase the diameter of the vasculature in the second treatment region; deflating the angioplasty balloon; advancing the shock wave device toward the angioplasty balloon until the angioplasty balloon is received within the inner tube and the shock wave device is aligned with the second treatment region; and activating the voltage source to apply shock waves to the second treatment region with the at least two electrodes.

Another variation of a method for delivering shock waves to treat vascular plaques includes introducing a shock wave device into a patient's vasculature; advancing the shock wave device within the vasculature toward a first treatment region; advancing an angioplasty balloon out of the inner tube and into the first treatment region; inflating the angioplasty balloon to increase the diameter of the vasculature in the first treatment region; deflating the angioplasty balloon; advancing the shock wave device toward the angioplasty balloon until the angioplasty balloon is received within the inner tube and the shock wave device is aligned with the first treatment region; and activating the voltage source to apply shock waves to the first treatment region with the at least two electrodes. In some examples, the method further includes advancing the angioplasty balloon out of the inner tube and into a second treatment region; inflating the angioplasty balloon to increase the diameter of the vasculature in the second treatment region; deflating the angioplasty balloon; advancing the shock wave device toward the angioplasty balloon until the angioplasty balloon is received within the inner tube and the shock wave device is aligned with the second treatment region; and activating the voltage source to apply shock waves to the second treatment region with the at least two electrodes. In other examples, the method further includes advancing the shock wave device and angioplasty balloon toward a second treatment region; advancing the angioplasty balloon out of the inner tube and into the second treatment region; inflating the angioplasty balloon to increase the diameter of the vasculature in the second treatment region; deflating the angioplasty balloon; advancing the shock wave device toward the angioplasty balloon until the angioplasty balloon is received within the inner tube and the shock wave device is aligned with the second treatment region; and activating the voltage source to apply shock waves to the second treatment region with the at least two electrodes.

BRIEF DESCRIPTION OF THE DRAWINGS

FIGS. 6A and 6B depict another variation of how inner electrodes and/or wires may be retained in a shock wave device.

DETAILED DESCRIPTION

Described herein are devices, systems, and methods that comprise one or more shock wave electrodes suitable for use in vasculature procedures. The shock wave electrodes may be disposed between a pair of concentric tubes that may act as a catheter. In some vat lotions, the pair of concentric tubes carry an additional treatment appliance (e.g., an angioplasty balloon). The volume between the pair of concentric tubes may be filled with a fluid (e.g., saline and/or imaging contrast agent). The shock wave electrodes within the pair of concentric tubes may be attached to a source of high voltage pulses, ranging from 100 to 10,000 volts for various pulse durations. This may generate a gas bubble at the surface of the electrode causing a plasma arc of electric current to traverse the bubble and create a rapidly expanding and collapsing bubble, which in turn creates a mechanical shock wave in the pair of concentric tubes. Shock waves may be mechanically conducted through the fluid and through the outer tube to apply mechanical force or pressure to break apart any calcified plaques on, or in, the vasculature walls. The size, rate of expansion and collapse of the bubble (and therefore, the magnitude, duration, and distribution of the mechanical force) may vary based on the magnitude and duration of the voltage pulse, as well as the distance between a shock wave electrode and the return electrode. Shock wave electrodes may be made of materials that can withstand high voltage levels and intense mechanical forces (e.g., about 1000-2000 psi or 68-136 ATM in a few microseconds) that are generated during use. For example, shock wave electrodes may be made of stainless steel, tungsten, nickel, iron, steel, and the like.

Figure 1A:
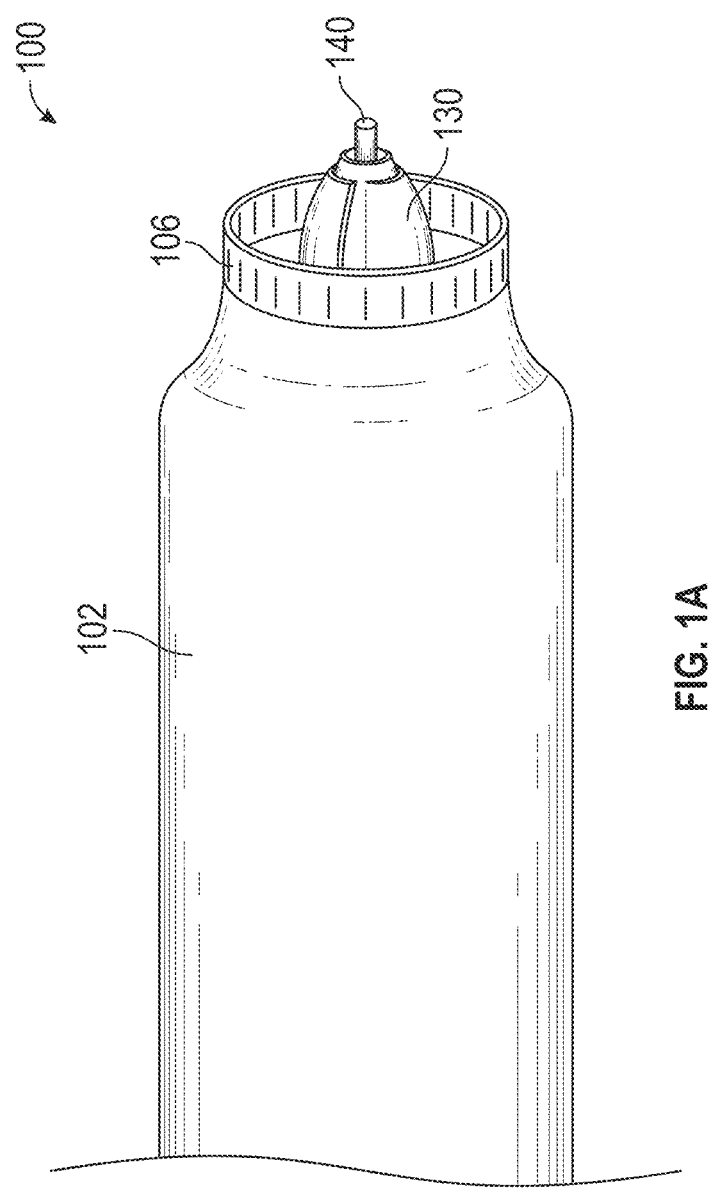
FIG. 1A depicts an example of a shock wave device comprising a pair of elongated, flexible concentric tubes.

FIG. 1A depicts an example of a shock wave device 100 comprising a pair of elongated, flexible concentric tubes. The pair of concentric tubes include an inner tube 104 (shown in FIG. 1C) and an outer tube 102. The pair of concentric tubes have a fluid input end located near a proximal end of the pair of concentric tubes (not shown), and a treatment end 106 located near a distal end of the pair of concentric tubes. The inner tube 104 and the outer tube 102 are connected together at the treatment end 106. In one preferred embodiment, the inner tube 104 and the outer tube 102 are bonded to each other at the treatment end 106 to form a sealed treatment end 106. The sealed treatment end 106 may allow a conductive fluid to be contained in the volume between the inner tube 104 and outer tube 102. In an alternate embodiment, the inner tube 104 and the outer tube 102 may include a fluid outlet port at the treatment end 106 to allow the conductive fluid to pass into the vasculature. A lumen extends through the center of the pair of concentric tubes. In some variations, a treatment appliance 130 (e.g., an angioplasty balloon) may be located within the lumen. A guide wire 140 may allow a practitioner to guide the pair of concentric tubes and/or treatment appliance 130 into a desired position (e.g., by guiding the pair of concentric tubes to a treatment area, and extending the treatment appliance 130 from the pair of concentric tubes, as shown in FIG. 1C). In this way, the pair of concentric tubes may act as a catheter carrying the treatment appliance 130 to a treatment area of a patient. While FIG. 1A shows the treatment appliance 130 (e.g., angioplasty balloon) within the inner tube 104 of the shock wave device 100, it should be understood that the treatment appliance 130 is optional and the shock wave device 100 may be utilized independently.

Figure 1B:
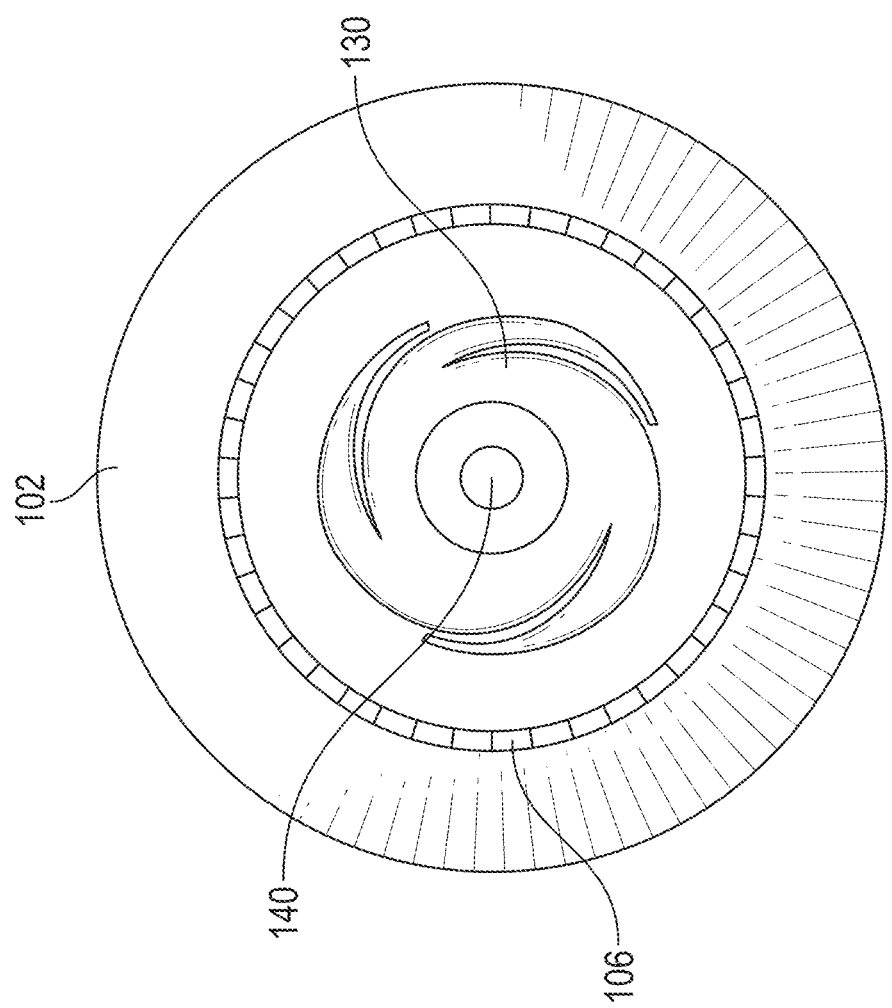
FIG. 1B depicts a front view of the shock wave device comprising a pair of elongated, flexible concentric tubes.
Figure 1C:
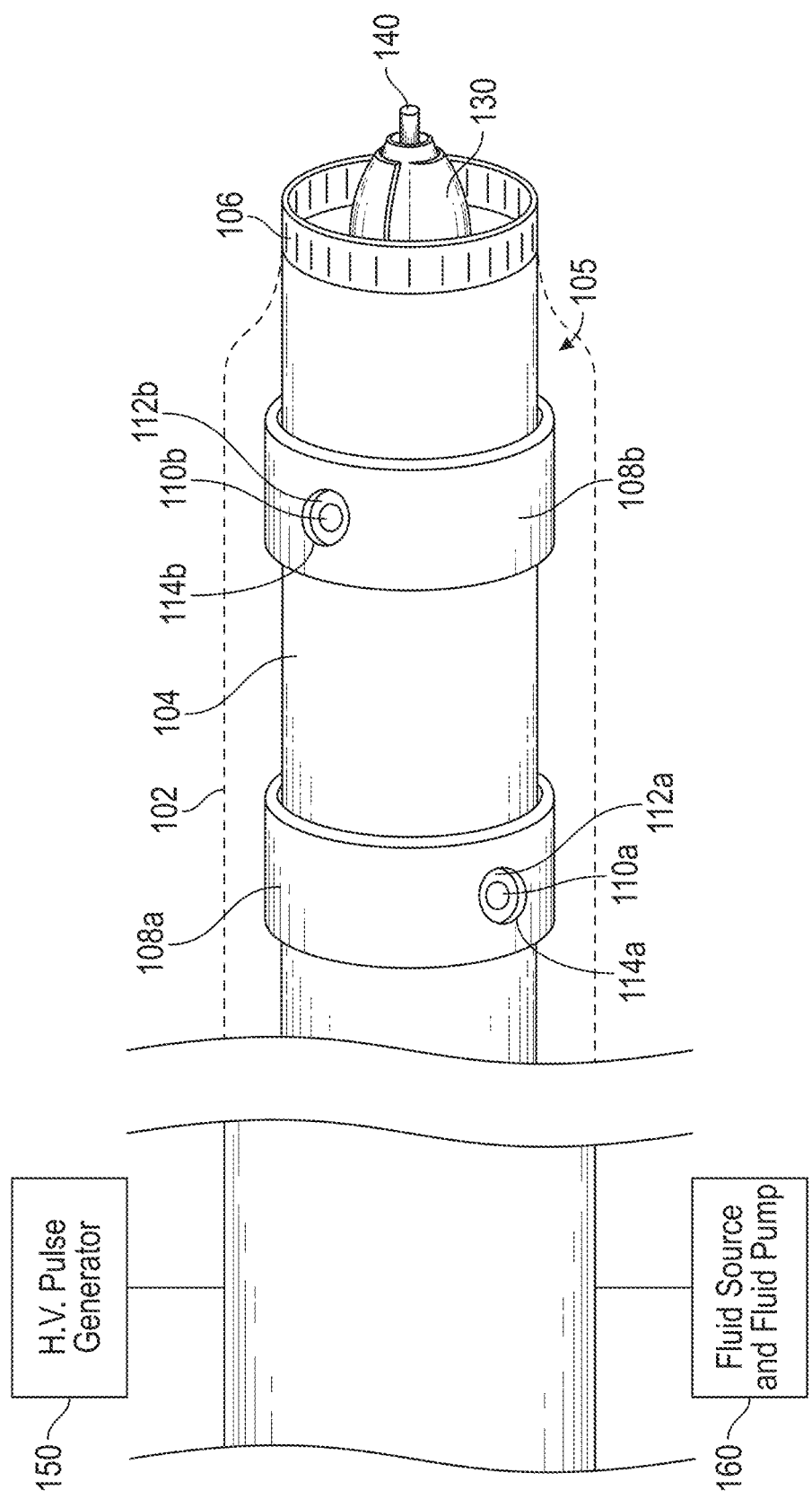
FIG. 1C depicts an interior volume of the shock wave device comprising a pair of concentric tubes.
Figure 1D:
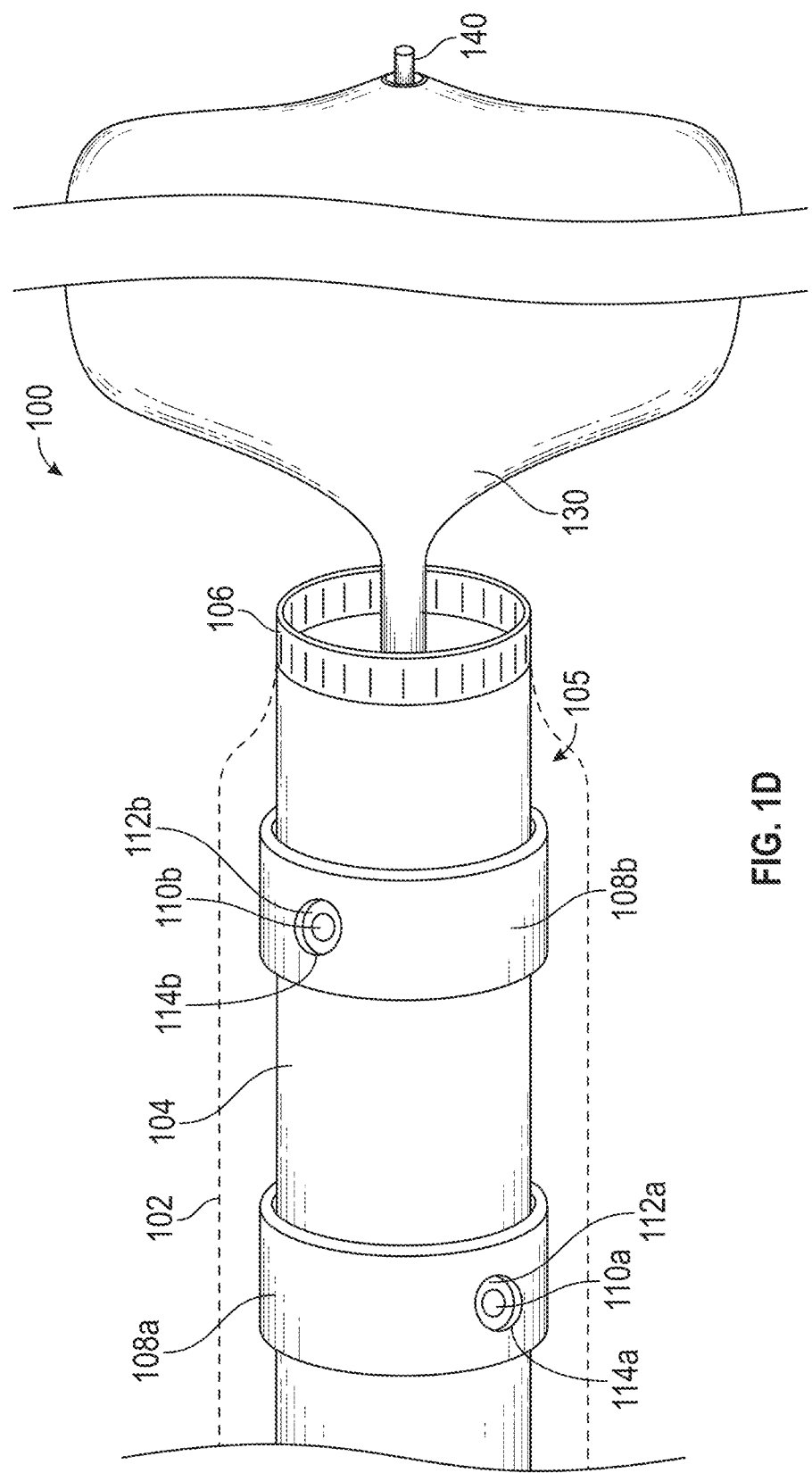
FIG. 1D depicts the shock wave device with an inflated treatment appliance extending from the central lumen of the pair of concentric tubes.
Figure 1E:
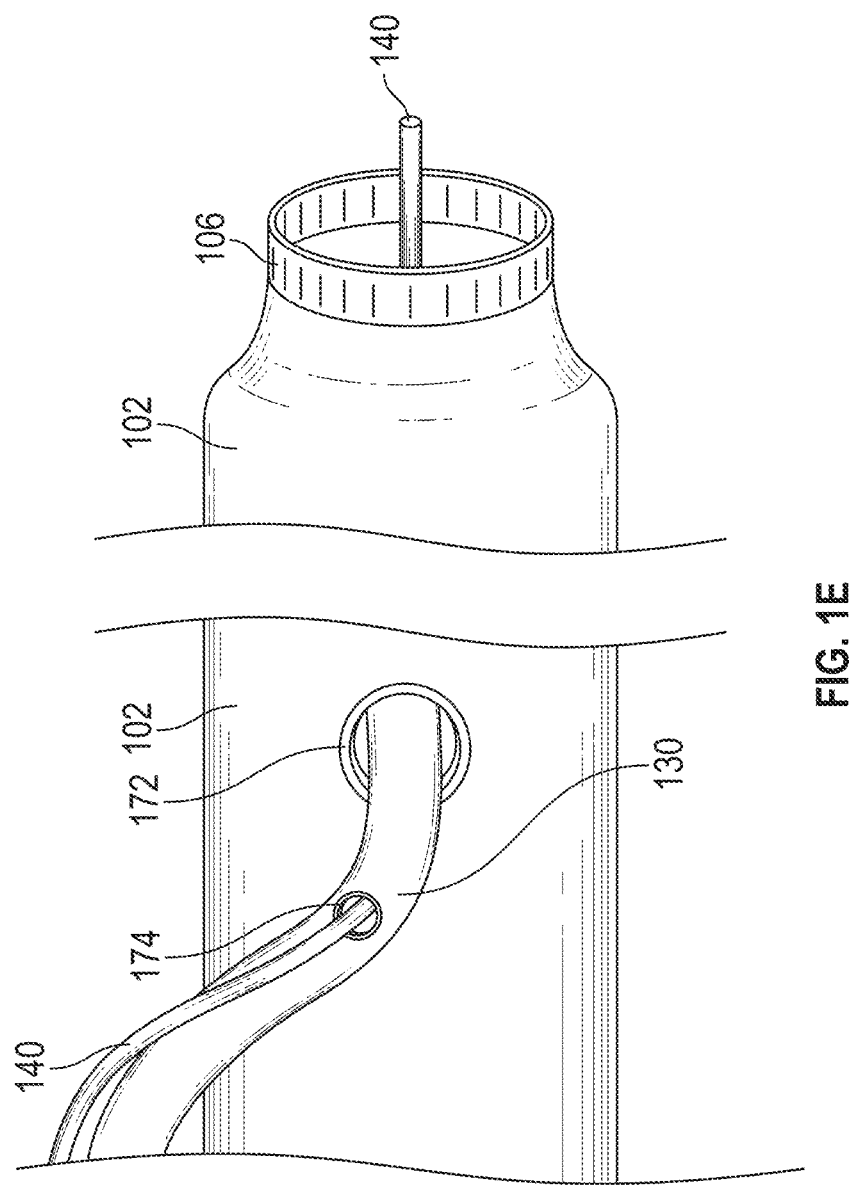
FIG. 1E depicts an exterior view of a shock wave device with a port in the pair of concentric tubes.

FIG. 1B depicts a front view of the shock wave device 100 comprising the pair of elongated, flexible concentric tubes. An optional treatment appliance 130 may be located within the central lumen of the pair of concentric tubes. As shown in FIG. 1B, the treatment appliance 130 may comprise an angioplasty balloon. The angioplasty balloon shown in FIG. 1B is deflated and folded upon itself to allow the balloon to be inserted into a port 172 of the shock wave device (as shown in FIG. 1E) and advanced through the central lumen of the pair of concentric tubes. The angioplasty balloon may be guided into position by the guide wire 140. After the balloon is extended out of the central lumen of the pair of concentric tubes, it may be inflated as shown in FIG. 1D.

As shown in FIG. 1C, a volume 105 between the inner tube 104 and the outer tube 102 may be filled with a conductive fluid via the proximal fluid input end of the pair of concentric tubes. The conductive fluid may be contained in the volume between the inner tube 104 and outer tube 102, or the conductive fluid may pass through a fluid outlet port at the treatment end 106. A fluid pump and fluid source 160 may be connected to the fluid input end to supply the conductive fluid to the volume 105. Shock wave electrodes are also positioned between the inner tube 104 and the outer tube 102. The shock wave electrodes are electrically connected to a high voltage pulse generator 150 located at the proximal end of the pair of concentric tubes. The shock wave electrodes are configured to generate shock waves in the conductive fluid in response to voltage pulses from the generator 150.

The shock wave electrodes may be low-profile or coplanar electrodes, such as those described in U.S. Pat. No. 8,888,788 and U.S. Publication No. 2017/0135709, which are hereby incorporated by reference in their entireties. In one variation, as shown in FIG. 1C, the shock wave electrodes may include inner electrodes 110a and 110b, outer electrodes 108a and 108b, and insulating sheaths 112a and 112b between the inner and outer electrodes. The outer electrodes 108a, 108b and insulating sheaths 112a, 112b may include apertures 114a, 114b aligned with the corresponding inner electrodes 110a, 110b, so that when a voltage is applied across the inner and outer electrodes, shock waves will be initiated from the location of the apertures 114a, 114b, as further described in reference to FIGS. 2A-D below. Alternatively, in another variation, the shock wave electrodes may be coplanar electrodes as described in reference to FIGS. 7-13 below.

Since the magnitude, duration, and distribution of the mechanical force impinging on a portion of tissue depends at least in part on the location and distance between the shock wave source and the tissue portion, a shock wave device having multiple shock wave electrodes at various locations along its longitudinal length may help to provide consistent or uniform mechanical force to a region of tissue. Thus, a plurality of shock wave electrodes may be distributed across the shock wave device (e.g., along a longitudinal length of the pair of concentric tubes) to minimize the distance between the shock wave source(s) and the tissue location being treated. For example, a calcified region of a vein or artery may extend over some longitudinal distance of the vein or artery, and a point source shock wave electrode would not be effective across the full extent of the calcified region because of the varying distance from the shock wave source to the various portions of the calcified region. Described herein are shock wave devices that comprise a plurality of low-profile or coplanar shock wave electrodes located along a longitudinal length of the pair of concentric tubes to distribute shock waves across a length of calcified vasculature. The low-profile or coplanar shock wave electrodes may be located along the diameter of the inner tube 104. The pair of concentric tubes may also be sized and shaped to distribute shock wave forces to a non-linear anatomical region. For example, the pair of concentric tubes may be curved, having a radius of curvature that approximates the radius of curvature of a valve (e.g., an aortic valve) or other vasculature. For example, a shock wave device 100 with a curved pair of concentric tubes may be suitable for applying shock waves to break calcified plaques in the vicinity of a valve and/or valve leaflets as part of a valvuloplasty procedure.

FIG. 1D depicts the shock wave device with the treatment appliance 130 extended from the central lumen of the pair of concentric tubes. The treatment appliance 130 may be guided into position by the guide wire 140. In one variation, as shown in FIG. 1D, the treatment appliance 130 comprises an angioplasty balloon, which is inflated after extending from the pair of concentric tubes. As shown in FIG. 1D, the angioplasty balloon may be inflated and may have a diameter larger than the diameter of the outer tube 102.

The pair of concentric tubes may be guided to a treatment area with the guide wire 140. The shock wave electrodes may then be activated, or the treatment appliance 130 may be extended from the pair of concentric tubes to another region of a patient's vasculature. For example, when the treatment appliance 130 comprises an angioplasty balloon, the balloon may be extended from the pair of concentric tubes, and then at least partially inflated. Inflating the balloon may increase the diameter of the treatment area. The balloon may then be deflated, and the pair of concentric tubes advanced toward the balloon to reach the treatment region of the patient's vasculature. As the pair of concentric tubes are advanced, the inner tube 104 may envelop the deflated balloon, causing the balloon to be received back within the central lumen of the pair of concentric tubes. Alternatively, the balloon may be advanced further into the patient's vasculature and re-inflated. The shock wave electrodes within the pair of concentric tubes may be used at various times during this procedure to generate shock waves to soften and/or loosen and/or remove plaques in the patient's vasculature.

FIG. 1E depicts an exterior view of a shock wave device with a port 172 in the pair of concentric tubes for inserting a guide wire 140, a treatment appliance 130, and/or other devices. In some examples, the treatment appliance 130 includes a second port 174 for inserting the guide wire 140 and/or other devices. The ports 172 and 174 may be a rapid exchange ports. While shown with a treatment appliance 130 (e.g., an angioplasty balloon) in FIG. 1E, it should be understood that the shock wave device can be utilized independently of the treatment appliance 130. In some examples, the port 172 allows a treatment appliance 130 (e.g., an angioplasty balloon) to be inserted into the pair of concentric tubes, and subsequently into the patient's vasculature, during a treatment procedure, as necessary. In this way, a practitioner has the option to utilize different treatment appliances 130 during a procedure (e.g., angioplasty balloons having different inflated diameters, lengths, or other properties).

Figure 1F:
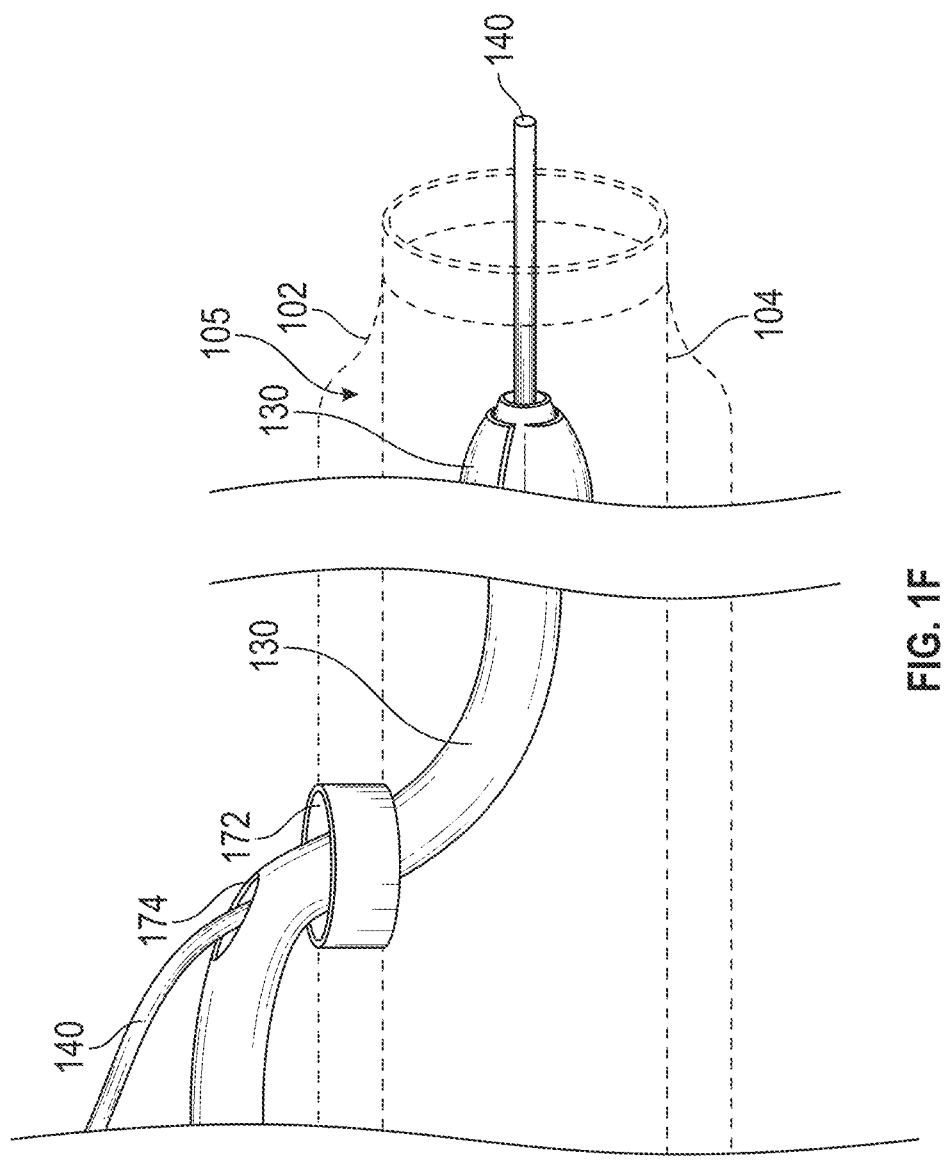
FIG. 1F depicts an interior view of the shock wave device with a port in the pair of concentric tubes.

FIG. 1F depicts an interior view of the shock wave device with a port 172 in the pair of concentric tubes. As shown in FIG. 1F, the port 172 extends between the pair of concentric tubes, allowing the treatment appliance 130, guide wire 140, or other device to access the interior of the inner tube 104. While the port 172 is shown as a cylindrical ring connecting the walls of the inner tube 104 and outer tube 102 in FIG. 1F, the port 172 may have other shapes. For example, the port 172 may be a slanted cylindrical ring that is angled to allow the treatment appliance 130 and/or guide wire 140 to access the lumen of the inner tube 104 at a shallower angle. Alternatively, the port 172 may be a thin ring that bonds the wall of the inner tube 104 to the wall of the outer tube 102.

The treatment appliance 130 may be an angioplasty balloon. In some examples, the treatment appliance 130 (e.g., angioplasty balloon) includes a second port 174 for inserting the guide wire 140 and/or other devices. The treatment appliance 130 (e.g., angioplasty balloon), guide wire 140 and/or other device may be inserted into the shock device subsequent to the shock wave device being introduced into the patient's vasculature. The ports 172 and 174 may be rapid exchange ports. In one example, an angioplasty balloon may be inserted within the inner tube 104 of the shock wave device through the port 172 and advanced through the inner tube 104 along the guide wire 140 to a treatment region. In some examples, a used angioplasty balloon may later be removed from the patient's vasculature through the port 172, and a new angioplasty balloon may be inserted to treat additional treatment regions.

Figure 2A:
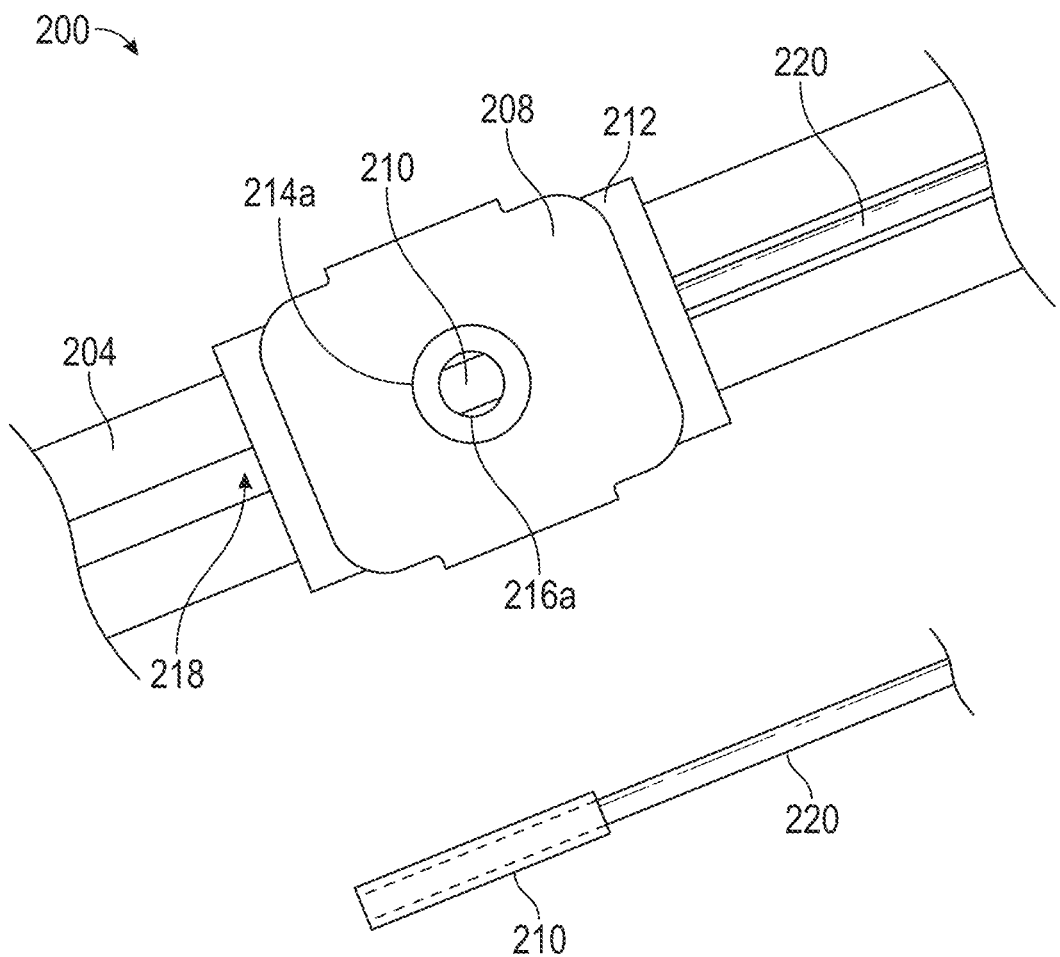
FIG. 2A depicts a top view of one variation of a low-profile shock wave electrode assembly and one variation of an inner electrode.

FIG. 2A depicts a variation of a shock wave electrode assembly 200 that may be used in any of the shock wave devices described herein. The electrode assembly 200 may include a first inner electrode 210, an insulating layer or sheath 212 disposed over the first inner electrode 210 and circumferentially wrapped around an inner tube 204, and an outer electrode 208 circumferentially disposed over the insulating sheath 212. While the insulating sheath 212 is depicted as fully circumscribing the inner tube 204, it should be understood that in other variations, an insulating layer may not fully circumscribe the inner tube 204, and may instead be disposed over certain portions of the first inner electrode 210 or inner tube 204. The insulating sheath 212 may have a first opening 216*a* that is coaxially aligned over the first inner electrode 210, and the outer electrode 208 may have a first opening 214*a* that is coaxially aligned over the first opening 216*a* of the insulating sheath 212. The electrode assembly 200 may also include a second inner electrode that is circumferentially opposite (or otherwise displaced from) the first inner electrode 210 (and therefore not depicted in the view shown in FIG. 2A). The insulating sheath 212 may have a second opening that is coaxially aligned over the second inner electrode, and the outer electrode 208 may have a second opening that is coaxially aligned over the second opening of the insulating sheath 212. The first inner electrode 210 coaxial with the first openings 214*a* and 216*a* in the insulating sheath 212 and the outer electrode 208 may generate a first shock wave that propagates outwards in a first direction and the second inner electrode coaxial with the second openings in the insulating sheath 212 and the outer electrode 208 may generate a second shock wave that propagates outwards in a second direction that is opposite to the first direction. The diameter of the openings in the outer electrode 208 may be larger than the diameter of the openings in the insulating sheath 212. The size of and ratio between the diameter of the openings in the outer electrode 208 and the openings in the insulating sheath 212 may be adjusted to attain the desired shock wave characteristics. The edges of the openings in any of the outer electrodes described herein may be electropolished.

Some variations of the electrode assembly 200 may not have an insulating sheath 212 disposed over the inner tube 204, but may instead include an inner electrode 210 having an insulating coating directly applied over the inner electrode. The insulating coating may cover the inner electrode such that a region of the conductive portion of the inner electrode is exposed, while the rest of the inner electrode is covered by the coating. The opening in the outer electrode 208 may be coaxially aligned with the exposed region of the inner electrode 210. The thickness and/or material of the insulating coating may be varied depending on the magnitude of the voltage to be applied across the electrodes. Examples of insulating coatings may be Teflon, polyimide, etc. Using an insulating coating on the inner electrode 210 instead of an insulating layer disposed over the inner tube 204 may further reduce the crossing profile of the electrode assembly 200, and may allow for more bending or a tighter turning radius than an electrode assembly having an insulating sheath 212.

The inner electrode 210 and the outer electrode 208 may each be connected to a high voltage pulse generator via a plurality of wires 220 that may be located within a plurality of longitudinal grooves 218 along the outer surface of the inner tube 204. The wires 220 may be electrically insulated along its length (e.g., by an insulating coating or sheath made of, for example, polyimide, PEBA, PET, FEP, PTFE, etc.) except for one or more regions where electrically conductive cores of the wires 220 are exposed to contact a portion of the inner electrode 210 and/or outer electrode 208. For example, the insulating coating or sheath at the distal tip of a wire may be stripped to expose the conductive portion. The wires 220 may be made of any conductive material, for example, free oxygen copper or copper or silver. The inner electrode 210 may be a hypotube that is crimped over a distal tip of one of the wires 220. The hypotube may be made of stainless steel, tungsten, a platinum-iridium alloy, or any other material with similar hardness.

In variations of the electrode assembly 200 without an insulating sheath 212 disposed over the elongate member, a portion of the inner electrode 210 may be coated with an insulating material as described above. Each groove 218 in the outer wall of the inner tube 204 may partially enclose a single wire. For example, wire 220 may be half enclosed within groove 218 in the outer wall of the inner tube 204, such that half of the wire 220 is recessed or embedded within the groove 218 and half of the wire 220 protrudes outside of the groove 218. The wire 220 may be slidably disposed within the groove 218. As the pair of concentric tubes are curved or bent (e.g., during an angioplasty procedure where the pair of concentric tubes act as a catheter that is advanced through a patient's vasculature), the wire 220 may slide within the groove 218 to accommodate changes in the radius of curvature as the pair of concentric tubes bends, thereby minimally interfering with the flexibility of the tubes. Optionally, one or more shrink tubes may be provided to retain the wire 220 within the groove 218 without impinging on its ability to move and shift as the pair of concentric tubes bend or curve. For example, one or more bands of shrink tubes may be located circumferentially around the inner tube 204. Alternatively or additionally or optionally, dots of epoxy may be applied along a length of the wire 220 to partially secure or retain the wire 220 within the groove 218 while still maintaining the ability of the wire 220 to partially move and shift as the pair of concentric tubes bend or curve. In some variations, the wire 220 may slide within the groove 218 without any retaining elements. Additional details regarding the longitudinal grooves of the inner tube are provided below.

Figure 2B:
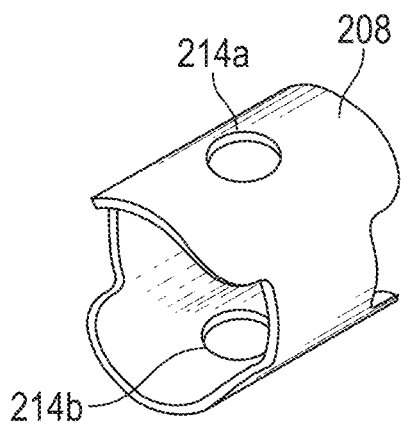
FIGS. 2B and 2C depict various views of one variation of an outer electrode of a shock wave electrode assembly.
Figure 2C:
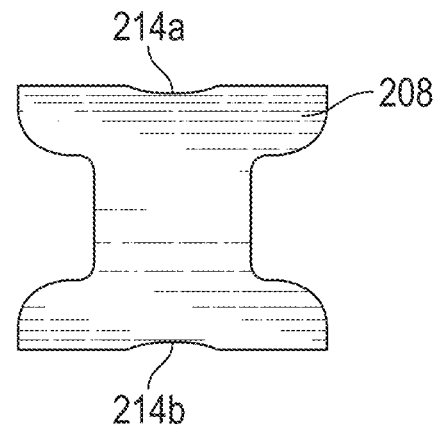

FIGS. 2B and 2C depict perspective and side view of the outer electrode 208. In some variations, the outer electrode 208 may be a radiopaque marker band (e.g., a marker band used in angioplasty procedures). As depicted in FIGS. 2B and 2C, the first opening 214*a* may be located directly across from the second opening 214*b*.

Figure 2D:
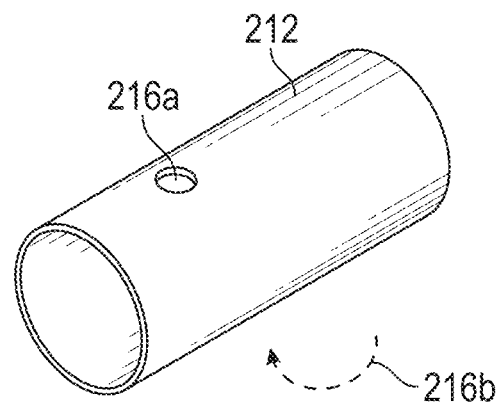
FIG. 2D depicts one variation of an insulating sheath of a shock wave electrode assembly.

FIG. 2D depicts a perspective view of the insulating sheath 212 having a first opening 216*a* and a second opening 216*b* located directed across from the first opening 216*a*. As described above, each of these openings may be coaxially aligned with the openings of the outer electrode 208 and first and second inner electrodes to form two shock wave sources capable of generating two shock waves that propagate outward from the side of the pair of concentric tubes in two opposite directions.

Figure 3A:
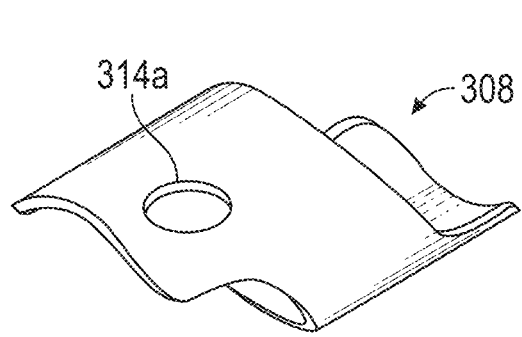
FIGS. 3A, 3B, and 3C depict other variations of an outer electrode and insulating sheath.
Figure 3B:
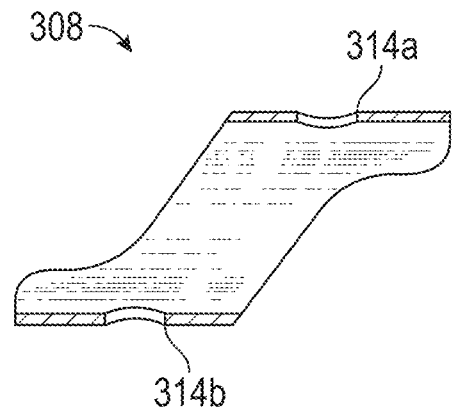

FIGS. 3A and 3B depict another variation of an outer electrode 308 that includes two openings 314*a* and 314*b* that are circumferentially across each other, but laterally offset. The diameter of each of the openings 314*a*, 314*b* may be from about 0.010 inch to about 0.024 inch, e.g., about 0.014 inch.

Figure 3C:
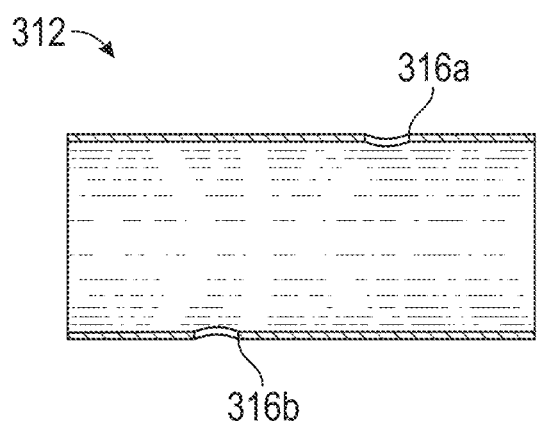

FIG. 3C depicts a variation of an insulating sheath 312 that comprises two openings 316*a* and 316*b* that are circumferentially across each other, but laterally offset. The diameter of each of the openings 316a, 316b may be from about 0.004 inch to about 0.01 inch, e.g., about 0.008 inch. The openings 314a, 314b of the outer electrode 308 may be coaxially aligned with the openings 316a, 316b of the insulating sheath 312, respectively. The outer electrode 308 and the insulating sheath 312 may be used with a pair of inner electrodes that are similarly circumferentially across each other, but laterally offset such that the two inner electrodes are each coaxially aligned with the each of the openings in the insulating sheath 312 and the outer electrode 308. This may functionally create two shock wave sources configured to generate two shock waves that propagate outward in two directions that are opposite each other but laterally offset.

Figure 4A:
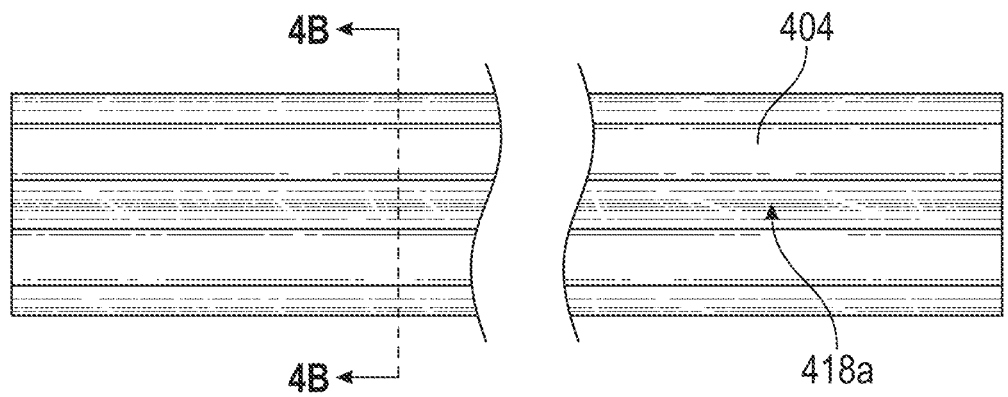
FIG. 4A depicts a side view of an inner tube of a shock wave device.
Figure 4B:
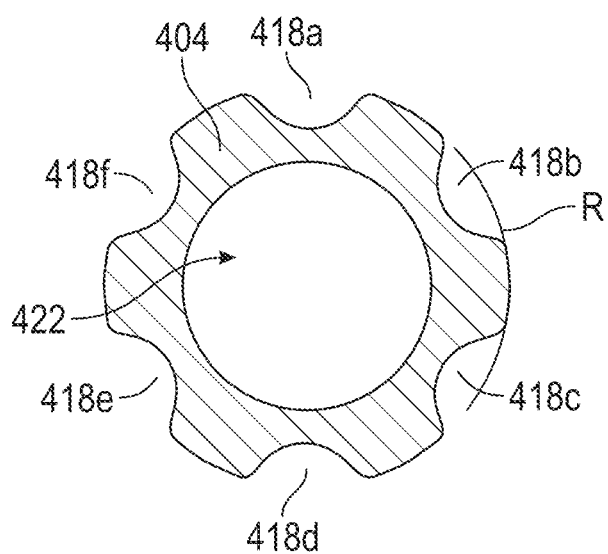
FIG. 4B is a cross-sectional view of the inner tube of FIG. 4A.

FIGS. 4A and 4B depict side and cross-sectional views (taken along line 4B-4B) of one variation of a grooved inner tube 404 that may be used in any of the shock wave devices described herein. The inner tube 404 may have any number of longitudinal grooves or channels along its outer surface configured for retaining wires and/or inner electrodes, and may for instance have 1, 2, 3, 4, 5, 6, 7, 8, 10, etc. grooves. As illustrated in FIG. 4B, the inner tube 404 has six grooves 418a-418f that surround a guide wire lumen 422. In some variations, the inner tube 404 may have a radius of about 0.014 inch and the each of the grooves 418a-418f may have a radius of curvature of about 0.005 inch to about 0.010 inch. Where the grooves 418a-418f may have a semi-elliptical shape, the minor axis may be about 0.008 inch and the minor axis may be about 0.015 inch. The inner tube 404 may also comprise a guide wire lumen 422, where the guide wire lumen may have a radius of about 0.0075 inch to about 0.018 inch, e.g., about 0.02 inch or 0.0175 inch.

Optionally, shrink tubing may be provided over each of the wires to help retain the wire within the groove while still allowing the wires to slide and move within the grooves to accommodate bending of the inner tube 404. Wires slidably disposed within longitudinal grooves on the outer surface of the inner tube 404 may retain the flexibility of the pair of concentric tube such that the pair of tubes may easily navigate and access tortuous vasculature. While the variations here depict wires that are slidably disposed within grooves of the elongate member to accommodate bending of the inner tube 404, in other variations, the wires may be conductive elements that are co-extruded with the inner tube 404 and therefore unable to slide with respect to the inner tube 404. However, co-extruding conductive elements with the inner tube 404 may stiffen the inner tube 404, thereby limiting its flexibility and ability to navigate to and access tortuous vasculature. For example, the smallest radius of curvature attainable by a tube with co-extruded conductive elements may be larger than the smallest radius of curvature attainable by a tube with wires slidably disposed in grooves along its outer surface. The turning radius of a tube that has wires slidably disposed within longitudinal grooves along its outer surface may be tighter than the turning radius of the same tube if the wires were unable to slide with respect to the tube.

The wires retained within the longitudinal grooves of the inner tube 404 may be connected to inner electrodes, as described above, and/or may be connected to outer electrodes. A wire that is retained within a longitudinal groove may be connected to an outer electrode using any suitable method, for example, by friction fit and/or adhesives. For example, the wire may be friction fit between the outer electrode and the insulating sheath, and optionally further secured in contact with the outer electrode with an adhesive.

Figure 5A:
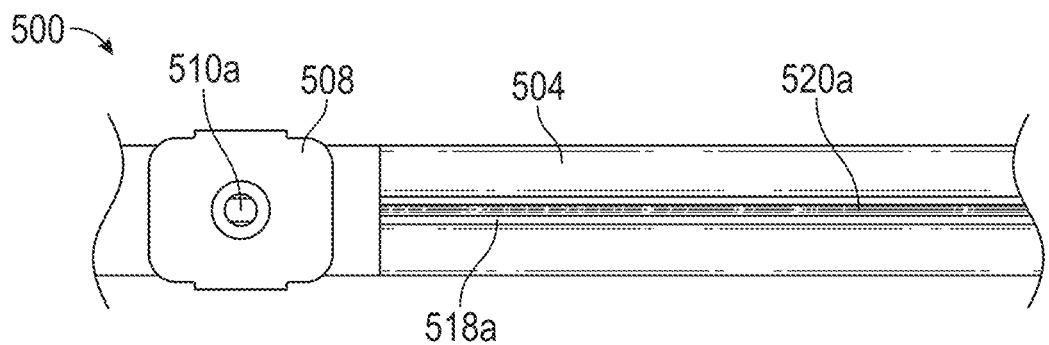
FIGS. 5A, 5B, and 5C depict one variation of how inner electrodes and/or wires may be retained in a shock wave device.
Figure 5B:
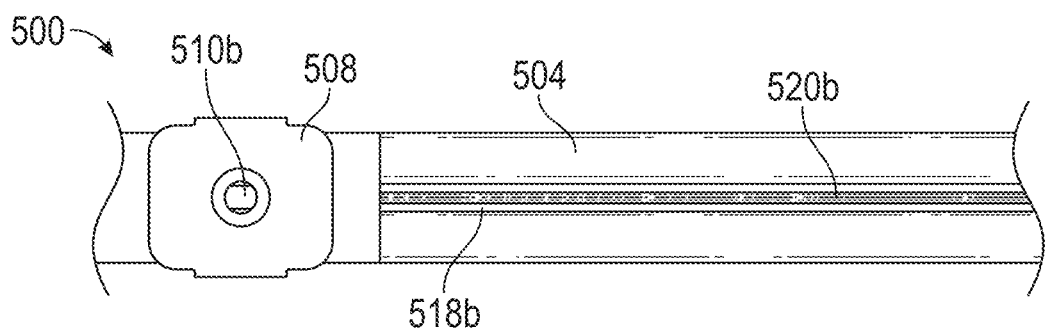
Figure 5C:
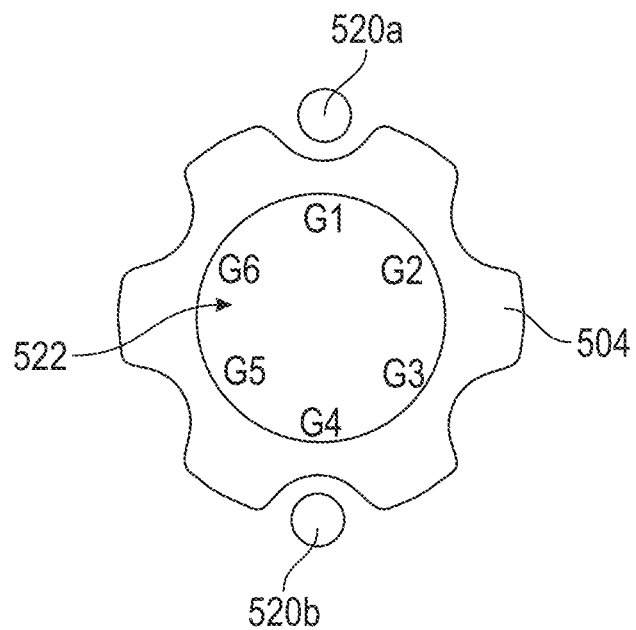

FIGS. 5A-5C depict one variation of how inner electrodes and/or wires may be retained in a shock wave device that comprises the shock wave electrode assembly 500. The shock wave device may include an inner tube 504 with a central guide wire lumen 522 and six longitudinal grooves (G1-G6) arranged around the guide wire lumen 522. FIG. 5A is a top view of the electrode assembly 500 where the first inner electrode 510a is visible and FIG. 5B is a bottom view of the electrode assembly 500 where the second inner electrode 510b is visible. The first and second inner electrodes 510a, 510b are located circumferentially opposite each other (i.e., 180 degrees apart). FIG. 5C depicts the grooves in which each of the inner electrodes and/or wires may be retained. The wire 520a connects the first inner electrode 510a with a first voltage output, and may be retained in groove 518a (G1). The wire 520b connects the second inner electrode 510b with the same or another voltage output, and may be retained in groove 518b (G4), directly opposite groove 518a (G1). While the example depicted here uses grooves G1 and G4, it should be understood that any two of the six grooves may be used to retain the wires 520a, 520b. For example, the wires 520a, 520b may be retained in grooves G2 and G5 respectively, or grooves G3 and G6 respectively, etc.

Some variations of shock wave devices may comprise two or more shock wave electrode assemblies. FIGS. 6A-6B depict a variation of two shock wave electrode assemblies 600a, 600b of a shock wave device. The first and second inner electrodes of each electrode assembly 600a, 600b may be connected to the same or separate voltage channels. The shock wave electrode assemblies 600a, 600b may be any of the electrode assemblies described herein. The first shock wave electrode assembly 600a may comprise a first inner electrode 610a, a second inner electrode (not shown) and an outer electrode 608a. The second shock wave electrode assembly 600b may comprise a first inner electrode 610c, a second inner electrode (not shown) and an outer electrode 608b. As shown in FIG. 6A, the first electrode assembly 600a and the second electrode assembly 6000b are each at different longitudinal locations along the inner tube 604.

As shown in FIG. 6B, the shock wave device may include an inner tube 604 with a central guide wire lumen 622 and six longitudinal grooves (G1-G6) arranged around the guide wire lumen 622. For each electrode assembly 600a, 600b, the first and second inner electrodes may be located circumferentially opposite each other (i.e., 180 degrees apart). FIG. 6B depicts the grooves in which each of the inner electrodes and/or wires may be retained, some of which are also depicted in FIG. 6A. Wire 620a connects the first inner electrode 610a of the first electrode assembly 600a with a voltage source, and may be retained in groove G1. Wire 620b connects the second inner electrode of the first electrode assembly 600a with the voltage source, and may be retained in groove G4, directly opposite groove G1. Wire 620c connects the first inner electrode 610b of the second electrode assembly 600b with the voltage source, and may be retained in groove GG2. Wire 620d connects the second inner electrode of the second electrode assembly 600b with the voltage source, and may be retained in groove G5, directly opposite groove G2. A return wire 620e may be connected to the outer electrode 608a, 608b and may be retained in groove G3. While the example depicted here uses grooves G1-G5, it should be understood that any five of the six grooves may be used to retain the wires. For example, the wires 620a-620e may be retained in grooves G1, G4, G2, G5, G3 respectively, or grooves G5, G3, G1, G4, G5 respectively, etc.

As depicted in FIG. 6A, the circumferential locations of the inner electrodes of the first electrode assembly 600a are different from the circumferential locations of the inner electrodes of the second electrode assembly 600b, i.e., they are offset from each other by an angle, which angle may be any value of about 1 degree to about 179 degrees, e.g., about 60 degrees, as determined by the locations of the grooves in which the inner electrodes are retained.

Figure 7:
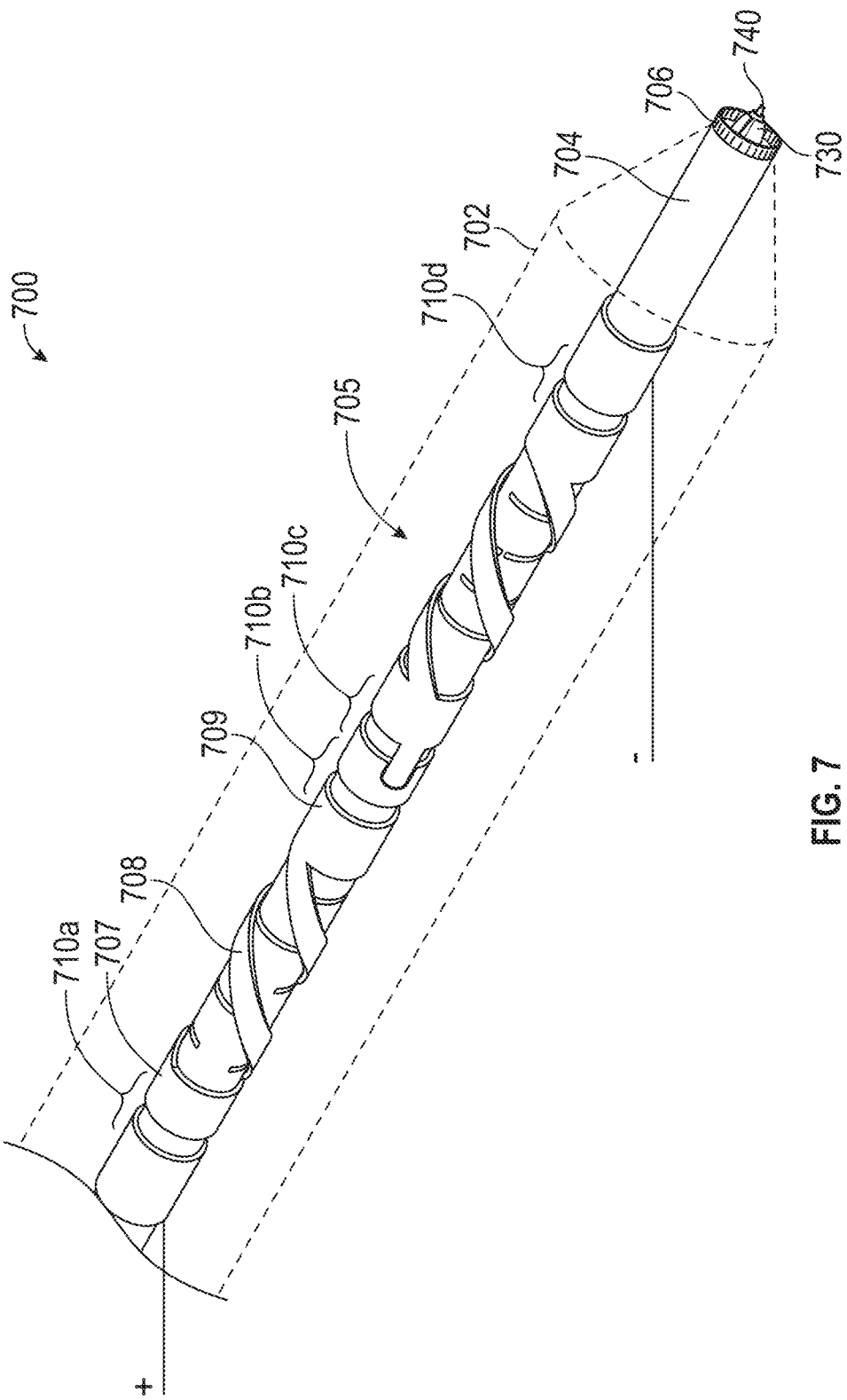
FIG. 7 depicts one variation of a shock wave device comprising single-layer, coplanar electrodes.

FIG. 7 depicts another variation of a shock wave device that comprises a first electrode that is circumferentially disposed over an outer surface of an inner tube, and a second electrode also circumferentially disposed over the outer surface of the inner tube, where a spark gap may be formed at the narrowest separation distance between the two electrodes. U.S. Publication Number 2017/0135709 further describes this variation, and is hereby incorporated by reference in its entirety. As shown in FIG. 7, the electrodes may be planar electrodes that are coplanar with each other (e.g., located along a single layer) over the outer surface of the inner tube. A first electrode may have a recess (or protrusion) that corresponds with a protrusion (or groove) of a second electrode. The separation between the edge of the recess (or protrusion) of the first electrode and the edge of the protrusion (or recess) of the second electrode may be the shortest distance between the first and second electrodes, and form the spark gap. Multiple pairs of these coplanar or single-layer electrodes may be arranged in series along the outer surface of the inner tube.

In a shock wave system, a voltage generator comprising a positive terminal and a negative terminal may be provided, and a first wire may connect the proximal-most electrode with the positive terminal and a second wire may connect the distal-most electrode with the negative terminal, without the need for additional interconnecting wires between the electrode pairs. Reducing the number of wires that extend along the length of the inner tube may help to maintain the flexibility and steerability of the overall shock wave device, which may facilitate the navigation of the shock wave device within tortuous vascular pathways. Reducing the number of wires along the length of the inner tube may also help reduce the thickness or diameter of the overall shock wave device. More generally, shock wave devices comprising the single-layer electrodes described in FIG. 7 (i.e., where the surfaces of the first and second electrodes are coplanar) may have a reduced thickness or diameter as compared to a shock wave device comprising stacked multi-layer electrodes (such as shown in FIG. 2A).

In multi-layer electrode designs, such as shown in FIG. 2A, shock waves are initiated by plasma arcs that extend across the insulating layer between the electrodes. However, for single-layer electrodes, the plasma arc extends across the spark gap between the electrodes along the outer surface of the inner tube, thereby eliminating the need for an additional insulating layer. Reducing the overall thickness of the electrode assembly and/or diameter of the shock wave device may allow the pair of concentric tubes to be navigated to smaller vascular structures for treatment.

In particular, FIG. 7 depicts an example of a shock wave device 700 that may be advanced into a patient's vasculature. The shock wave device 700 may include an inner tube 704, an outer tube 702, a treatment appliance 730 within a lumen of the inner tube 704, and one or more pairs of electrodes 710a-d enclosed between the inner tube 704 and the outer tube 702. In some variations, a single electrode may be part of two electrode pairs. For example, the proximal end 705 of electrode 707 is part of electrode pair 710a and the distal end 709 of electrode 707 is part of electrode pair 710b. The treatment appliance 730 may be collapsed and retained within the lumen of the inner tube 704 while the shock wave device 700 navigates through the vasculature, and advanced out of the inner tube 704 (as shown in FIG. 1C) after the shock wave device 700 is located at the desired treatment position.

The shock wave device 700 may be in communication with a fluid source that introduces fluid into a volume 705 between the inner tube 704 and outer tube 702. The shock wave device 700 may also comprise a voltage generator having a positive terminal and a negative terminal, and a first wire that connects that proximal-most electrode to the positive terminal and a second wire that connects the distal-most electrode to the negative terminal (of course, the polarity may be reversed). After the volume 705 between the inner tube 704 and outer tube 702 is filled with a fluid to a certain pressure, a voltage pulse may be applied to the electrodes, thereby generating one or more shock waves that may propagate through the fluid and the wall of the outer tube 702 to impinge on a calcification. Shock waves may be generated repeatedly, as may be desirable by the practitioner.

Although the shock wave device 700 is depicted as having four electrode pairs (e.g., electrode pairs 710a-d), it should be understood that other variations of shock wave catheters may have a different number of electrode pairs (e.g., 1, 2, 4, 5, 7, 8, 10, 12, 16, 20, etc.). In the description of shock wave devices and electrodes below, the outer tube 702 is not depicted, though such a tube may be included in any of the variations described herein.

In some variations, a coplanar shock wave electrode pair may comprise a first electrode comprising a protrusion and a second electrode comprising a recess that receives the protrusion, where a separation between the edge of the protrusion and the edge of the recess forms a spark gap. For example, the first electrode may comprise a recess and the second electrode may comprise a protrusion that is received by the recess such that the separation between the protrusion and the recess forms a spark gap. A spark gap is a separation between two electrodes across which a plasma arc is likely to form in the presence of a high voltage pulse across those electrodes. The protrusion and the corresponding recess may have any suitable geometry or shape, and may be, for example, shaped like a circle, oval, ellipse, square, hexagon, octagon, triangle, and the like. Protrusions and recesses may have corresponding arcuate shapes or curves. In some variations, the shape of the protrusion and the recess may be selected such that the separation between the first and second electrode is fairly uniform. For example, the protrusion may be circular, so that the distance between the edge of the circular protrusion to the edge of the recess in the second electrode that receives that protrusion may be substantially uniform. The shape of the protrusion and the recess may be selected such that the likelihood of a spark or arc forming at any location along the length of the spark gap is substantially the same. In some variations, the protrusion and the recess may be configured such that the likelihood of a spark forming between the protrusion and the recess is substantially uniform or equal along the length of the spark gap. For example, the protrusion and the corresponding recess may have a smooth contour (i.e., without acute angles, tight turns, or small radii of curvature) such as an arcuate or rounded curve. Arranging the electrodes such that the location of the spark along the spark gap is randomized may help to extend the life of the electrodes as compared to electrodes where the spark always occurs at the same location or region of the spark gap. By arranging the electrodes such that sparks originate at different locations along the gap, the wear on the electrode may be distributed along the gap instead of wearing down a single location along the gap. This may help to lengthen the life of the electrodes as compared to electrodes where sparks originate at the same location or region of the spark gap.

Some electrodes may have one protrusion on one side and one recess on another side (e.g., a protrusion on the proximal edge of the electrode and/or at a first radial position, a recess on the distal edge of the electrode and/or second radial position), and/or a first protrusion on one side and a second protrusion on another side (e.g., a first protrusion on the proximal edge of the electrode and/or at a first radial position, a second protrusion on the distal edge of the electrode and/or at a second radial position), and/or a first recess on one side and a second recess on another side (e.g., a first recess on the proximal edge of the electrode and/or at a first radial position, a second recess on the distal edge of the electrode and/or at a second radial position). In an electrode pair, the first electrode may comprise any number or combination of protrusions and/or recesses (such as those described above) while the second electrode may comprise a corresponding number or combination of recesses and/or protrusions that are complementary to the protrusions and/or recesses of the first electrode.

In some variations where the first and second electrodes have more than one pair of complementary protrusions and/or recesses between them, a spark or arc may form between only one of the protrusion/recess pairs at a time (e.g., per voltage pulse), and there may be some variability as to which of the protrusion/recess pairs will spark at a particular time. That is, the spark or arc will only happen at one of the protrusion/recess pairs, while the next spark or arc may be at another one of the protrusion/recess pairs. This variability may help to distribute the wear across the multiple protrusion/recess pairs so that the overall life and/or durability of the electrode pair is extended as compared to an electrode pair where all of the sparks are formed across the same protrusion/recess pair.

In some variations, the distal and/or proximal edges of the first electrode and the proximal and/or distal edges from the second electrode may have multiple undulating curves, lobes, peaks and troughs, such that the interface between them comprises a space (which may be a spark gap) that curves between the edges of the electrodes. The space between the two electrodes may have varying distances, which may in turn determine where a spark or plasma arc extends between the electrodes during the generation of a shock wave. For example, to reduce the likelihood that a spark occurs at a particular location between the two electrodes, the spacing at that location may be greater than the spacing in the surrounding areas. To increase the likelihood that a spark occurs at a particular location between the two electrodes, the spacing at that location may be less than the spacing in the surrounding areas. Examples of electrode pairs with varying degrees of separation are further described below.

In some variations, the electrodes may be coated with an insulating material in certain regions and not coated with insulating material (i.e., electrically exposed) in other regions. The location of the insulated regions and exposed regions may also help to increase the likelihood of generating a plasma arc in certain regions while decreasing the likelihood of generating a plasma arc in other regions. For example, insulating the region of the electrodes where the separation between the electrodes is narrow (e.g., may be the narrowest separation) may help to greatly reduce the likelihood of generating a plasma arc across the separation in this region, while exposing (i.e., not insulating) this region may increase the likelihood of generating a plasma arc. The location of a spark gap may be determined at least in part by the relative locations of insulated regions and exposed regions of the electrodes, as well as the size of the spacing/separation between the electrodes at the exposed regions. The location of spark gaps and the characteristics of the shock waves produced by the plasma arcs that span those spark gaps may be determined at least in part by the size, shape and location of the exposed regions of the electrodes.

Figure 8:
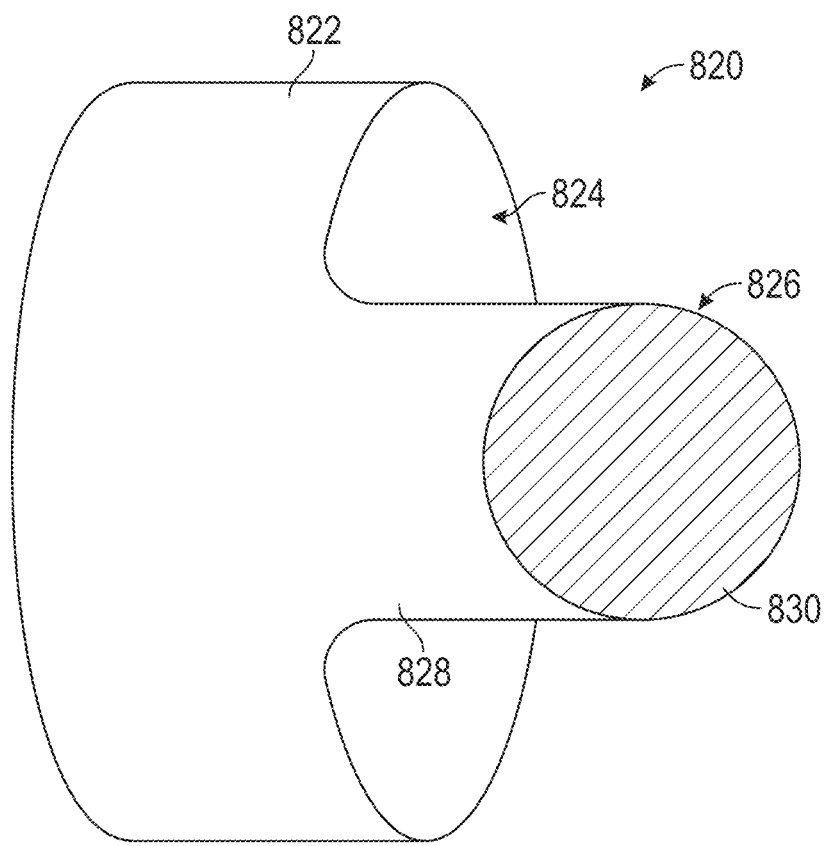
FIG. 8 depicts one variation of a single-layer electrode.

FIG. 8 depicts one variation of an electrode that may be used in any of the shock wave devices herein. Electrode 820 may be shaped as a cylindrical band configured to be disposed over the outer surface of an inner tube. Electrode 820 may comprise a sleeve 822 with a lumen 824 therethrough, and a protrusion 826 extending from the sleeve 822. The protrusion 826 may have any of the shapes described and depicted herein, and in the variation of FIG. 8, may comprise a stem portion 828 and a lobe 830 at the end of the stem. In this example, the shaded region of the lobe 830 may be exposed while the unshaded regions of the electrode 820 are covered by an insulating material. The lobe 830 may be the region of the electrode that interfaces with a recess of a second electrode that has exposed edges (e.g., may be substantially or entirely exposed), and the separation/spacing between the lobe and the edges of the recess may form a spark gap. Exposed or uninsulated regions of two electrodes in close proximity to each other may form a spark gap, regardless of the geometry of the electrodes. Optionally, the exposed regions of the electrodes may be treated (e.g., coated) to help enhance heat dissipation capabilities. For example, the exposed regions of any of the electrodes described herein may have a silver or gold coating. In the variations of shock wave devices described below, the protrusions or recesses of one electrode and the complementary recesses or protrusions of an adjacent electrode that interfaces with the first electrode may have exposed regions of electrically conductive material to form a spark gap at those interfaces. Teflon, Kapton, varnish or oxides and anodized insulations are just a few examples of many suitable insulation materials.

The relative surface area of the exposed regions of an electrode pair may also increase or decrease the likelihood of a spark or arc forming across the spacing/separation between electrodes. For example, the first electrode may have a first exposed region with a first surface area and the second electrode may have a second exposed region with a second surface area, and in some variations, the second surface area may be greater than the first surface area. For example, the ratio between the first surface area and the second surface area may be from about 1:2 to about 1:50, e.g., from about 1:2 to about 1:10, from about 1:4 to about 1:10, from about 1:2 to about 1:20, from about 1:10 to about 1:30, from about 1:20 to about 1:40, from about 1:30 to about 1:50. For example, the area of the first surface area (e.g., of the electrode with the smaller exposed region) may have a radius of about 0.008 inch, and the ratio between the first surface area and the second surface area may be about 1:4.

Figure 9A:
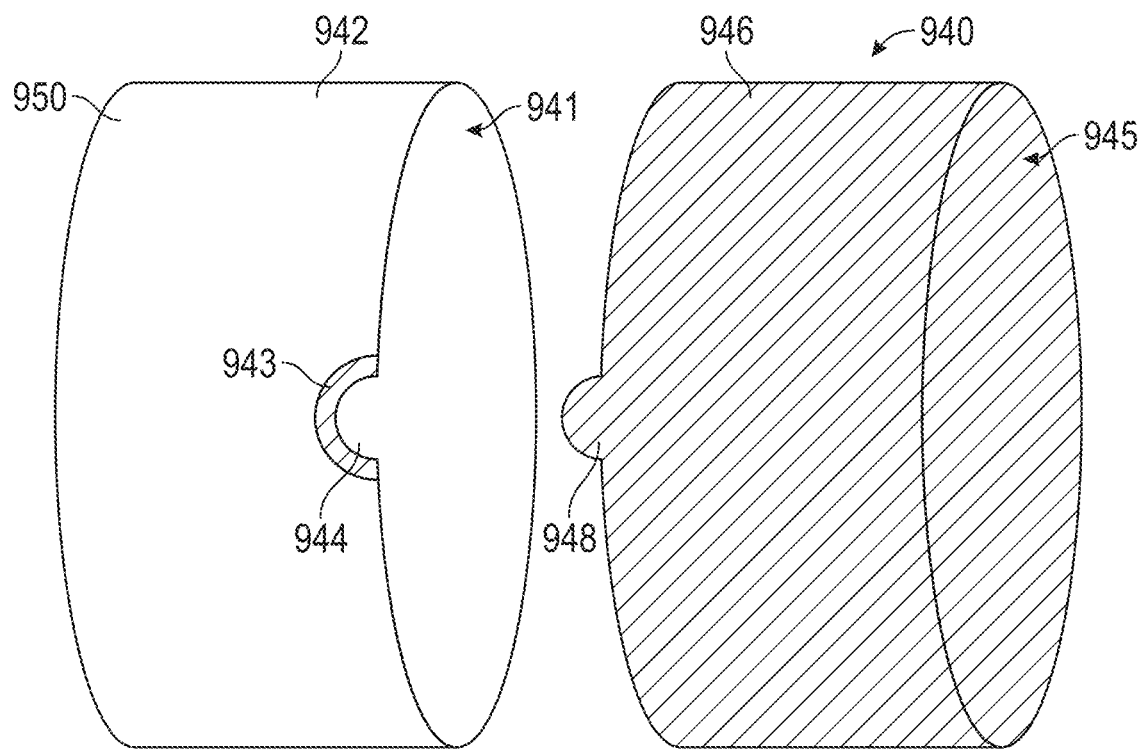
FIG. 9A depicts one variation of a pair of single-layer electrodes.

FIG. 9A depicts one variation of an electrode pair 940 comprising a first electrode 942 having a recess 944 and a second electrode 946 having a protrusion 948 that corresponds with the recess 944. In this example, the recess and protrusion both have arcuate shapes. The first electrode 942 and second electrode 946 may be tubular, each with a lumen 941, 945 therethrough configured to be disposed over the outer surface of an inner tube such that they are coplanar (e.g., in a single layer) around the inner tube. The shaded/patterned portions of the electrodes represent electrically exposed (i.e., uninsulated) regions of the electrodes and the unshaded portions represented electrically insulated regions. While the entire surface of the second electrode 946 may be exposed, a small region 943 of the first electrode 942 located around the edge of the recess may be exposed. The surface of the small region 943 is smaller than the surface area of the second electrode, and the ratio between them may be any of the ratios described above.

Figure 9B:
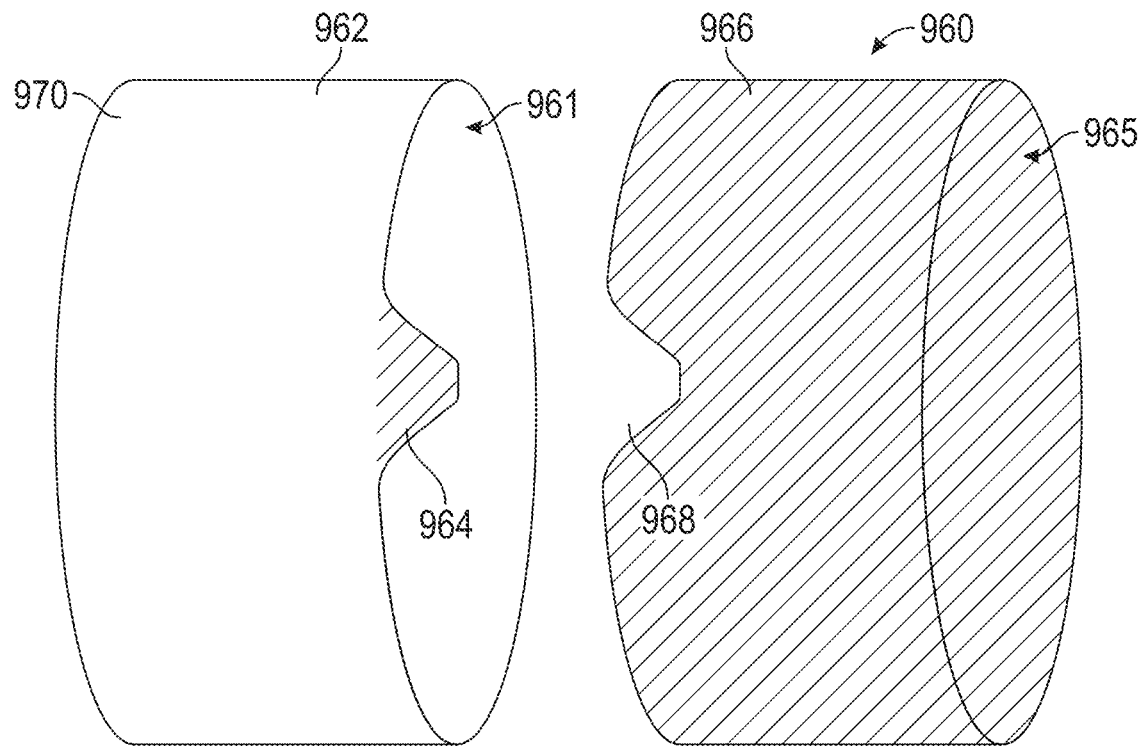
FIG. 9B depicts another variation of a pair of single-layer electrodes.

FIG. 9B depicts another variation of an electrode pair 960 comprising a first electrode 962 having a protrusion 964 and a second electrode 966 having a recess 968 that corresponds with the protrusion 964. In this example, the protrusion and the recess both have arcuate shapes. The first electrode 962 and second electrode 966 may be tubular, each with a lumen 961, 965 therethrough configured to be disposed over the outer surface of an inner tube such that they are coplanar (e.g., in a single layer) around the inner tube. While the entire surface of the second electrode 966 may be exposed, only the protrusion 964 of the first electrode may be exposed. The surface of the protrusion 964 is smaller than the surface area of the second electrode, and the ratio between them may be any of the ratios described above. Other variations with different areas and shapes of insulated and exposed electrode regions are described and depicted herein.

Figure 10A:
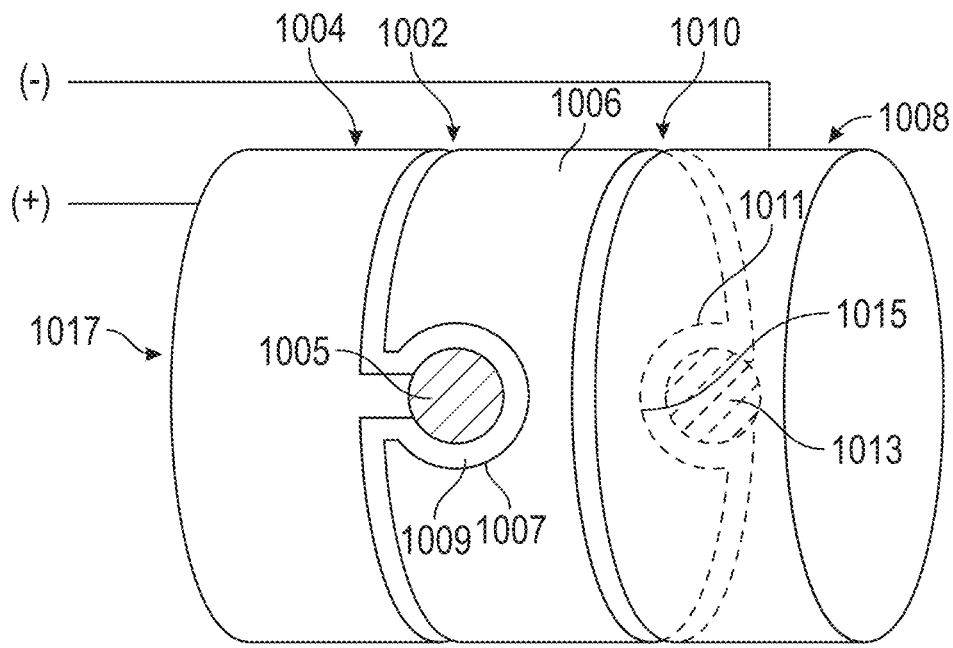
FIG. 10A depicts one variation of single-layer electrodes of a shock wave device that interfit with each other.

FIG. 10A depicts one example of two electrode pairs, where one electrode (e.g., the middle electrode) is a part of both pairs. The first electrode pair 1002 may comprise a first electrode 1004 and a second electrode 1006, and the second electrode pair 1010 may comprise the second electrode 1006 and a third electrode 1008. The first electrode 1004 may be electrically connected to the positive terminal of a voltage generator while the third electrode 1008 may be electrically connected to the negative terminal of a voltage generator (e.g., by a wire for each connection). The first, second, and third electrodes may be ring-shaped and have a lumen 1017 therethrough, and be disposed over the outer surface of an inner tube on a single-layer (i.e., the electrodes may be co-planar with each other over the outer surface of the inner tube).

The first electrode 1004 (i.e., the proximal electrode) may comprise a protrusion 1005 that has a stem and a circular lobe. The second electrode 1006 may comprise a recess 1007 that is sized and shaped to receive the protrusion 1005 such that there is a space or gap 1009 between the edge of the protrusion 1005 and the edge of the recess 1007. The second electrode 1006 and third electrode 1008 may have a similar interface on the opposite side of the system. That is, the second electrode 1006 may have a second recess 1011 and the third electrode 1008 may have a protrusion 1013 that is received by the second recess 1011 such that there is a space or gap 1015 between them. The protrusion 1013 may have a stem and a circular lobe similar in size and shape to the protrusion 1005, or may have a different size or shape, as may be desired.

The circular lobes of the protrusions 1005, 1013 and the edges of the recesses that receive the protrusions (recesses 1007, 1011) may be electrically exposed or conductive, while the remainder of the electrodes may be electrically insulated. In this variation, the entire surface of the second electrode 1006 may be exposed or uninsulated. As such, spark gaps may be formed at the interfaces of the protrusions and the recesses.

The location of the first protrusion 1005 and corresponding recess 1007 and the location of the second protrusion 1013 and corresponding recess 1011 may vary according to the desired initiation location of a shock wave. In this example, the first pair and second pair of protrusions/recesses are located radially opposite to each other, with the first pair located on a proximal edge of the electrode and the second pair located on a distal edge of the electrode. In other variations, the first and second pair may both be located on the proximal side (or the distal side) of the middle electrode 1006, but radially opposite each other. In some variations, the first and second pair may be radially offset with respect to each other, where the offset angle may be anywhere from about 30 degrees to about 180 degrees in either direction (clockwise or counterclockwise). In some variations, there may be more than one pair of protrusions/recess between each electrode pair. For example, the first electrode 1004 may have an additional protrusion or recess at a different radial location and the second electrode 1006 may have an additional corresponding recess or protrusion.

Optionally, different regions of each of the electrodes may be covered by an insulating material while other regions are exposed. For example, the portions of the protrusion 1005 and the protrusion 1013 that are shaded may be exposed, while the remainder of the electrode 1004 and the electrode 1008 may be covered by an insulating material. The second electrode 1006 may be entirely exposed and uninsulated. Alternatively, at least the regions around the edges of the recesses 1007 and 1011 may be exposed, while the remainder of the electrode may be insulated. The exposed regions may optionally have a silver or gold coating.

As described previously, the relative sizing of the surface area of the exposed regions between the electrodes in a pair may help to facilitate and guide the electric current flow between electrodes so that plasma arcs or sparks occur at the desired spark gap location. In some variations, the likelihood of creating a plasma arc that is capable of generating a shock wave is increased when the surface area of the exposed (i.e., uninsulated) region of a first electrode is smaller than the surface area of the exposed region of a second electrode that is adjacent to it. The exposed surface area differential may be represented by the ratio of the surface area of an exposed region of a first electrode to the surface area of an exposed region of a second electrode. The interface between an electrode pair described in any of the shock wave devices disclosed herein, regardless of their shape or location, may have the exposed surface area differential described above.

Figure 10B:
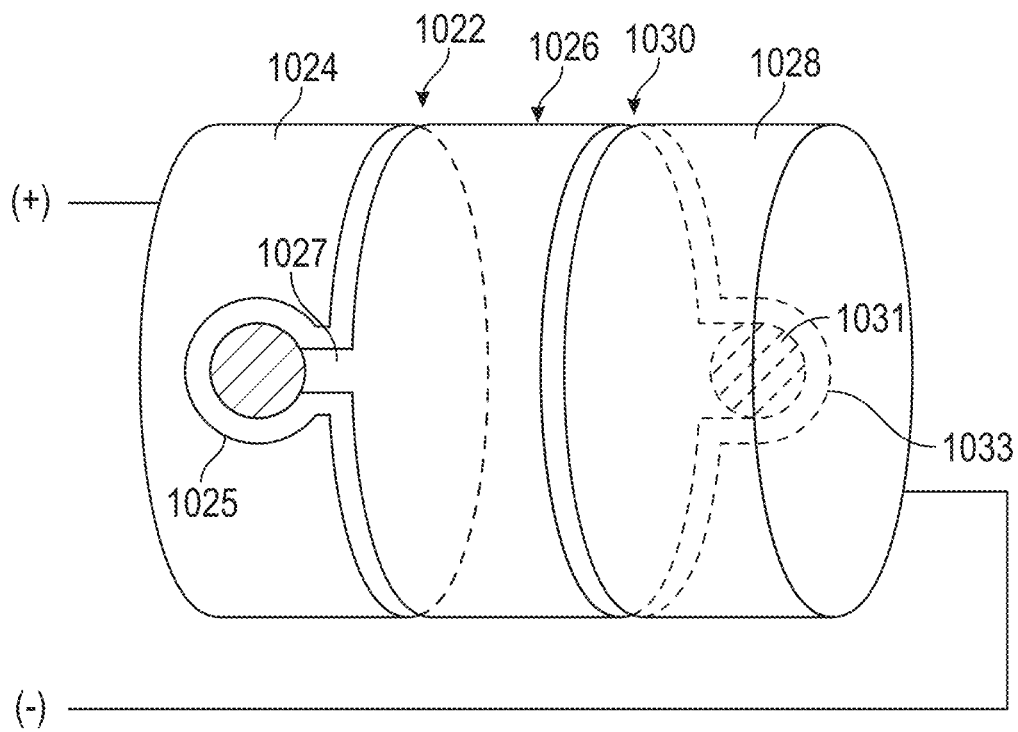
FIG. 10B depicts another variation of single-layer electrodes of a shock wave device that interfit with each other.

FIG. 10B depicts another variation of two electrode pairs that are similar to the electrode pairs depicted in FIG. 10A, except that where there was a protrusion, there is now a recess and where there was a recess, there is now a protrusion. For example, the first electrode pair 1022 comprises a first (proximal) electrode 1024 and a second (middle) electrode 1026. The first electrode 1024 comprises a recess 1025. The second (middle) electrode 1026 comprising a protrusion 1027 that is located within the recess 1025. The second electrode pair 1030 comprises the second electrode 1026 and a third (distal) electrode 1028. The second electrode 1026 comprises a second protrusion 1031. The third (distal) electrode 1028 comprises a recess 1033 within which the protrusion 1031 is located. In other words, instead of the middle electrode having two radially offset and opposite recesses as illustrated in FIG. 10A, the middle electrode now has two radially offset and opposite protrusions as illustrated in FIG. 10B.

The first electrode 1024 may be connected to the positive terminal of a voltage generator while the third electrode 1028 may be connected to the negative terminal of a voltage generator (e.g., by a wire for each connection). The various parameters and variants described above for FIG. 10A may also be applicable in the variation depicted in FIG. 10B.

Figure 10C:
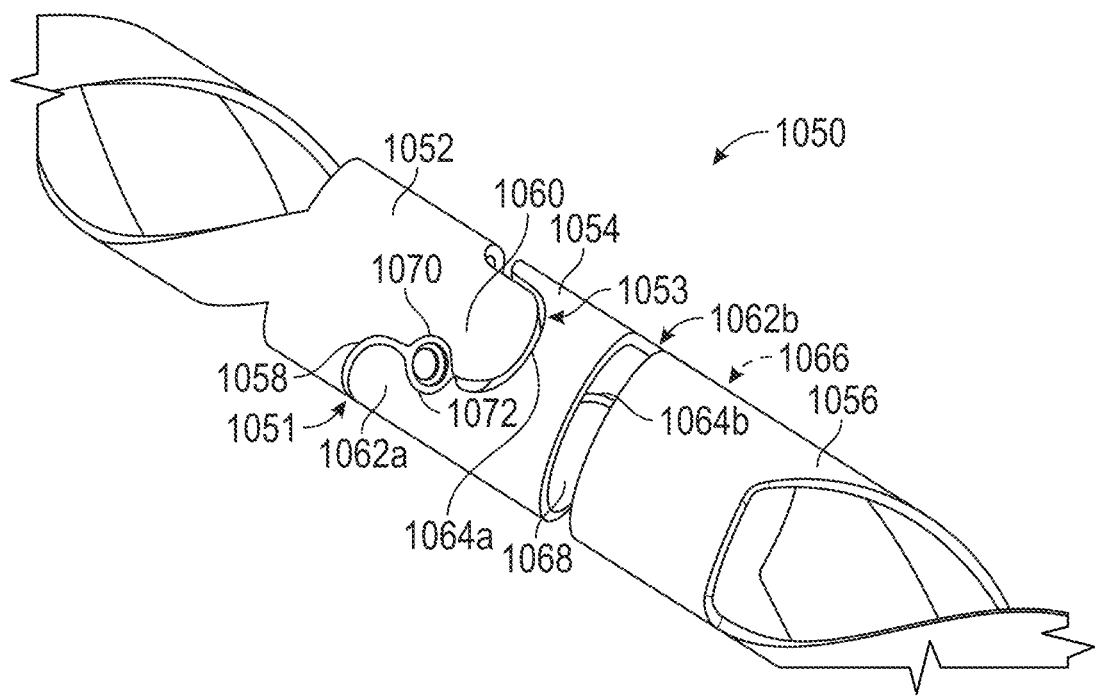
FIG. 10C depicts one variation of three single-layer electrodes that have multiple spark gaps per electrode pair.

FIG. 10C depicts an example of a shock wave device 1050 comprising a first electrode 1052, second electrode 1054, and third electrode 1056 (for clarity, the inner tube, outer tube, treatment appliance, and wiring of the device are not shown). The first, second and third electrodes are coplanar with each other, arranged on a single layer along the outer surface of the inner tube of the shock wave device. The first electrode 1052 may comprise a first recess 1058 and a first protrusion 1060. The second electrode 1054 may comprise a second protrusion 1062a, a second recess 1064a, a third protrusion 1062b opposite to the second protrusion 1062a, and a third recess 1064b opposite to the second recess 1064a. The third electrode 1056 may comprise a fourth recess 1066 and a fourth protrusion 1068. There may be two spark gaps located between the first and second electrodes, and two other spark gaps located between the second and third electrodes. In some variations, of the two spark gaps between an electrode pair, only one spark gap will form a plasma arc during a voltage pulse.

The location and arcuate curvature of the first recess 1058 may correspond with the location and arcuate curvature of the second protrusion 1062a to form a first spark gap 1051 therebetween, and the location and arcuate curvature of the first protrusion 1060 may correspond with the location and arcuate curvature of the second recess 1064a to form a second spark gap 1053 therebetween. Similarly, the location and arcuate curvature of the third recess 1064b may correspond with the location and arcuate curvature of the fourth protrusion 1068 to form a third spark gap 1055 therebetween, and the location and arcuate curvature of the third protrusion 1062b may correspond with the location and arcuate curvature of the fourth recess 1066 to form a fourth spark gap therebetween (not visible in this view).

While it may be desirable that some regions of the separation between the electrodes (i.e., the protrusions and recesses) form spark gaps where the likelihood of plasma arc formation is relatively high, there may be some electrode separation regions where it is desirable for the likelihood of plasma arc formation to be relatively low. One way of reducing the likelihood of forming a plasma arc at a particular separation region is to increase the distance between the two electrodes relative to the surrounding separation region. An example is depicted in FIG. 10C. The first electrode 1052 comprises a recess or groove 1070 and the second electrode 1054 comprises a recess or groove 1072 that is aligned with the groove 1070 of the first electrode 1052. Aligning two recesses or grooves may increase the width of the separation between the first electrode 1052 and second electrode 1054 relative to the width of the separation in the intended spark gap regions.

In some other variations, a first electrode may have a recess while the second electrode may have a straight edge (e.g., no protrusion) in the region of the recess. While the recesses are depicted as having an arcuate or curved shape, it should be understood that the recesses may have any shape. For example, a recess may have straight edges (e.g., a square shape, rectangular shape, triangular shape, etc.), and/or have curved edges (e.g., circle, oval, ellipse, semicircle, semi-oval, semi-ellipse, etc.), and/or a combination of straight and curved edges (e.g., rectangular, triangular or any polygon with rounded corners and/or undulating edges).

The increased separation between the electrodes provided by one or more recesses may help to reduce the likelihood of formation of a plasma arc at the recessed region(s). In some variations, one or both of the electrodes in a pair may have edge(s) that curve away from the edge of the other electrode. For example, the electrodes may have an undulating curved edge (comprising one or more concave or convex curves) where the peaks and troughs do not follow each other (e.g., are out-of-phase with each other). For example, one electrode may have a straight edge (i.e., without a recess or protrusion), while the other electrode may have undulating curves comprising a convex curve at a desired spark gap region and a concave curve in regions where no spark gap is desired. Alternatively or additionally to increasing the separation width in a region where no plasma arc is desired, such regions may be electrically insulated, which may also help to impede the formation of a plasma arc.

Figure 11A:
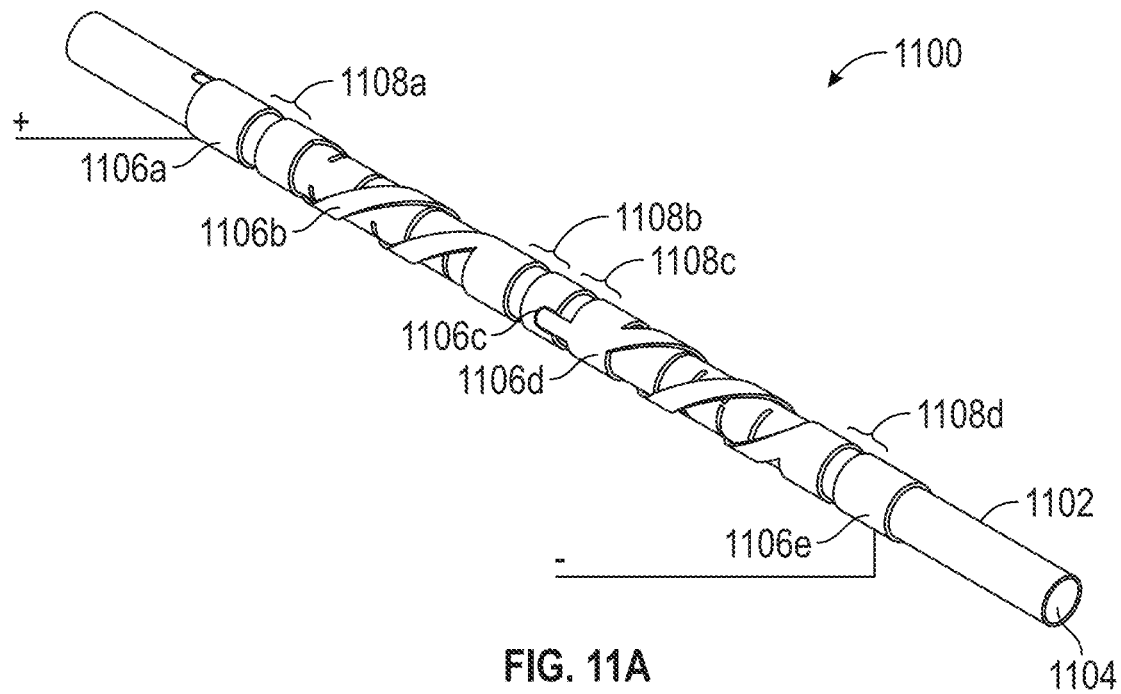
FIGS. 11A, 11B, and 11C depict another variation of a shock wave device having one or more single-layer electrodes.
Figure 11B:
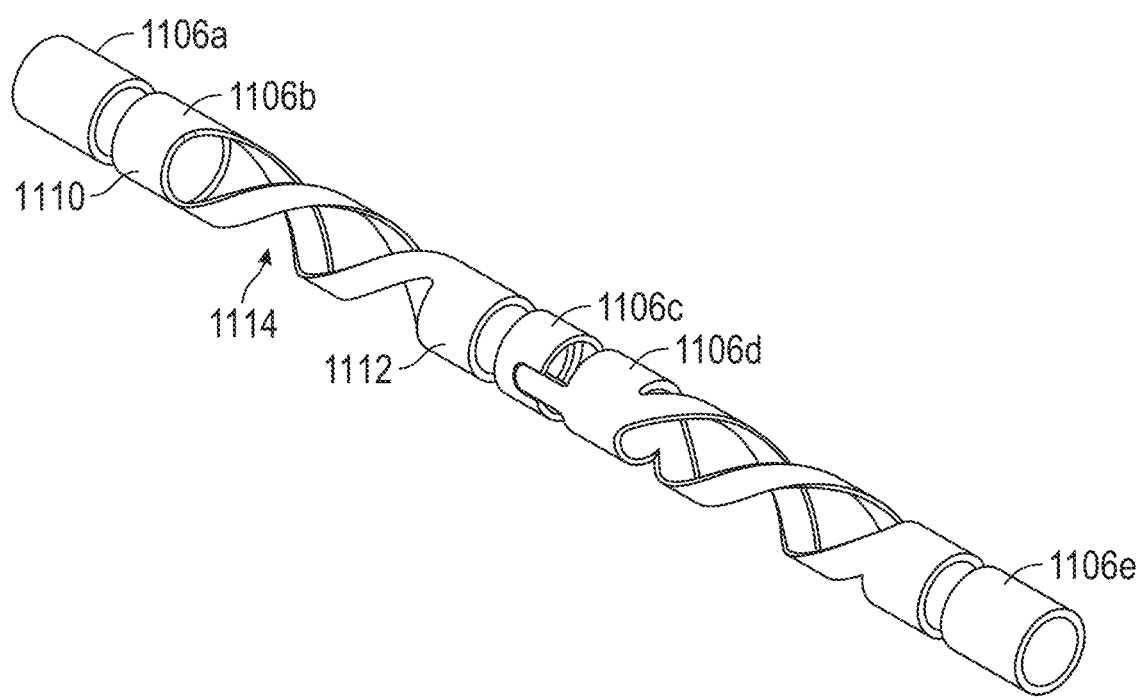
Figure 11C:
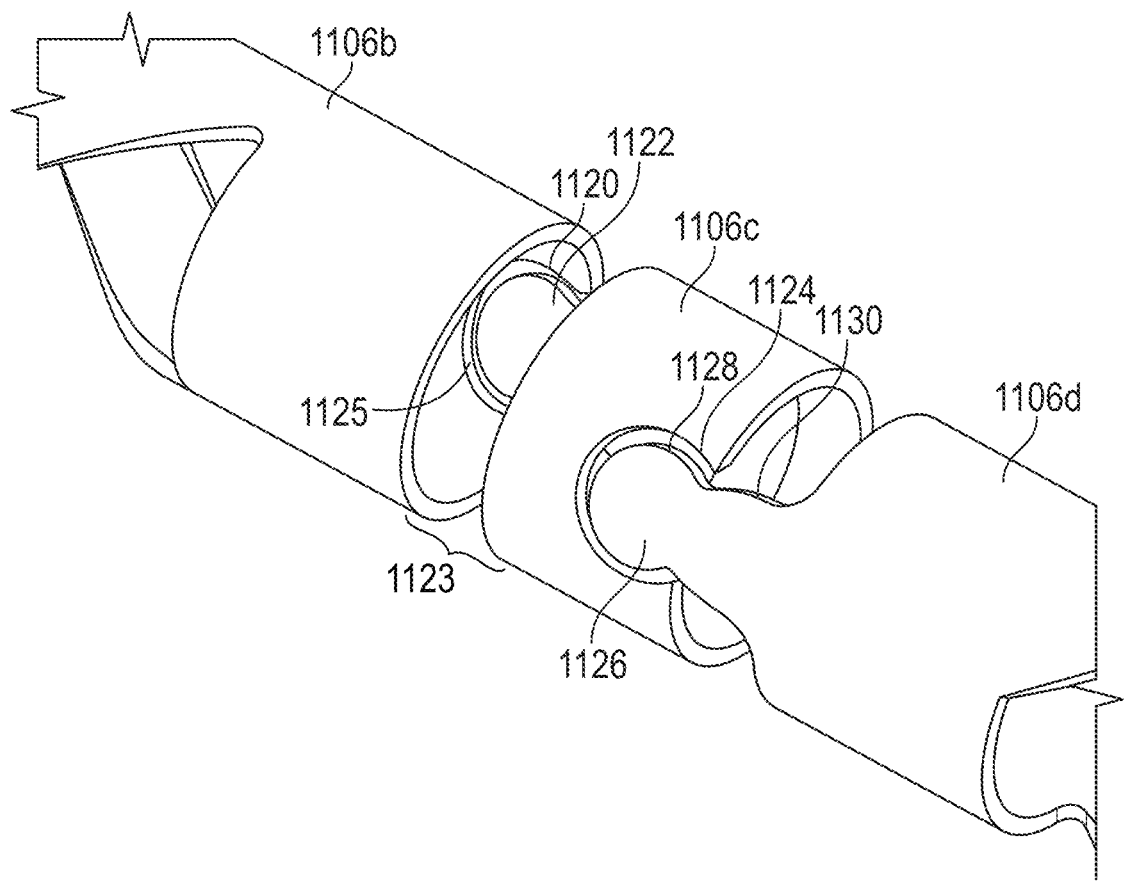

One variation of a shock wave device having one or more single-layer (i.e., co-planar) electrodes is depicted in FIGS. 11A-11C. The shock wave device 1100 may comprise an inner tube 1102, a lumen 1104, and five electrodes 1106a-e that form four electrode pairs 1108a-1108d. The shock wave device 1100 may also comprise an outer tube (not shown) that encloses the electrodes, a treatment appliance (not shown) movable through the lumen 1104, a first wire that connects the proximal-most electrode 1106a to a positive terminal of a voltage source and a second wire that connects the distal-most electrode 1106e to a negative terminal of a voltage source. As previously described, the volume between the inner tube 1102 and the outer tube is filled with a fluid medium before a voltage is applied across the electrodes for the generation of shock waves. The first and second wires may each extend along the outer surface and/or lumen and/or within the wall of the inner tube 1102.

Each electrode pair may have one or more spark gaps as may be desirable. For example, a first electrode pair may have one spark gap capable of initiating one shock wave, while a second electrode pair may have two spark gaps capable of initiating two shock waves (i.e., one shock wave per spark gap). In other examples, an electrode pair may have more than two spark gaps, and may have three, four, five or more spark gaps. When a voltage is applied across the proximal-most electrode 1106a and the distal-most electrode 1106e, a series of plasma arcs may form serially across the spark gaps between the electrodes (i.e., from electrode 1106a to electrode 1106b, from electrode 1106b to electrode 1106c, from electrode 1106c to electrode 1106d, from electrode 1106d to electrode 1106e, which then guides the current back to the negative terminal of the voltage source via the wire) to initiate a series of expanding shock waves. The number of initiated shock waves may correspond to the number of spark gaps between the electrodes (e.g., each spark gap gives rise to one plasma arc per voltage pulse and/or each plasma arc initiates one shock wave), and/or may be greater than (e.g., a spark gap may give rise to more than one plasma arc per voltage pulse, and/or each plasma arc initiates one or more shock waves) or less than (e.g., plasma arcs may not form across all of the spark gaps) the number of spark gaps.

FIG. 11B depicts the electrodes 1106a-e without other components of the shock wave device (such as an inner tube, outer tube, or treatment appliance). The length of each electrode with respect to each other may vary. For example, the proximal-most electrode 1106a and the distal-most electrode 1106e may be shorter than the second electrode 1106b and fourth electrode 1106d. The shortest electrode may be the center electrode 1106c. Electrodes whose lengths extend along a substantial segment of the inner tube may be configured such that their effect on the flexibility and bendability of the inner tube is reduced. For example, electrode 1106*b* (as well as electrode 1106*d*) may comprise a proximal portion (e.g., a band) 1110, a distal portion (e.g., a band) 1112, and a body portion 1114 extending between the proximal and distal portions. In this variation, the proximal and distal portions may be generally cylindrical or marker band-like structures. The body portion may be covered by an insulating material, which may help to facilitate current flow between the proximal and distal portions along the body portion. The structure of the body portion 1114 may be selected to help facilitate bending of the electrode 1106*b* as the inner tube bends.

In the variation depicted in FIGS. 11A-11C, the body portion 1114 may comprise a helical structure or spiral that wraps around the outer surface of the inner tube between the proximal and distal portions. The threads of the helical structure or spiral of the body portion 1114 may be selected in order to accommodate flexion, torqueing, and/or steering of the shock wave device. For example, the body portion 1114 may have a pair of spirals (e.g., a double-helix), where each spiral has one twist. In other variations, there may be more spirals (e.g., triple or quadruple helices), and/or each spiral may have more than one twist (e.g., two, three, four, five or more twists).

FIG. 11C is a close view of the interface between electrodes 1106*b-d*. In this variation, electrode 1106*b* has a recess 1120 that corresponds to a protrusion 1122 on electrode 1106*c* (which form electrode pair 1108*b*), and electrode 1106*c* has a recess 1124 that corresponds to protrusion 1126 on electrode 306*d* (which form electrode pair 308*d*). There may be a separation 1123 between electrodes 1106*b* and 1106*c*, where the narrowest portion of the separation 1123 may be a spark gap 1125. In this variation, the protrusions 1122, 1126 may have a circular lobular portion 1128 connected to a stem 1130. The stem 1130 may extend between the widest part of the separation 1123 between the electrodes, while the perimeter of the circular lobular portion 1128 may comprise at least a portion of the spark gap 1123. In this example, the protrusions and recesses for both electrode pairs have the same or similar shape and size, however, in other variations, the protrusions and recesses may have different shapes or sizes.

The electrodes 1106*b-d* may have electrically insulated regions and exposed (i.e., electrically non-insulated) regions, the location and sizing of which may be configured to help guide the direction of the current flow and/or to facilitate the formation of plasma arcs or sparks at the desired spark gap locations. In the variation depicted in FIG. 11C, the majority of the surface area of the electrode 1106*b* may be exposed or uninsulated, while the majority of the surface area of the electrode 1106*c* is insulated, except for the regions that are adjacent to the spark gap 1125. That is, the protrusion 1122 (e.g., the circular lobe of the protrusion) and the region along the edge of the recess 1124 of the electrode 1106*c* may be exposed, but the remainder of the electrode 1106*c* may be insulated (e.g., the stem portion of the protrusion, the cylindrical region or body of the electrode extending between the proximal and distal portions or bands of the electrode, the spiral or twisted region of the body, the body region between the proximal and distal portions or bands of the electrode, etc.). The circular lobular portion 1128 of the electrode 1106*d* may be exposed, while the stem portion 1128 and the body of the electrode (e.g., the portion extending between the proximal and distal ends) may be insulated. The surface area of the exposed portion of the electrode 1106*b* may be larger than the surface area of the protrusion 1122 that is exposed. For example, the ratio between the surface area of the exposed portion may be from about 1:2 to about 1:50, e.g., from about 1:2 to about 1:10, from about 1:2 to about 1:20, from about 1:10 to about 1:30, from about 1:20 to about 1:40, from about 1:30 to about 1:50. Similarly, the surface area of the circular lobular portion 1128 may be smaller than the surface area of the exposed region along the edge of recess 1124, and may have similar ratio values described above.

Some variations of electrodes may have a proximal portion with an exposed protrusion or recess edge, a distal portion with another exposed protrusion or recess edge, and a body portion between the proximal and distal portions that is insulated. The surface area of the one or more exposed regions of an electrode may affect the strength, shape, location, etc. of the plasma arc formed, which in turn affects the sonic output and/or direction of the initiated shock wave.

Figure 12:
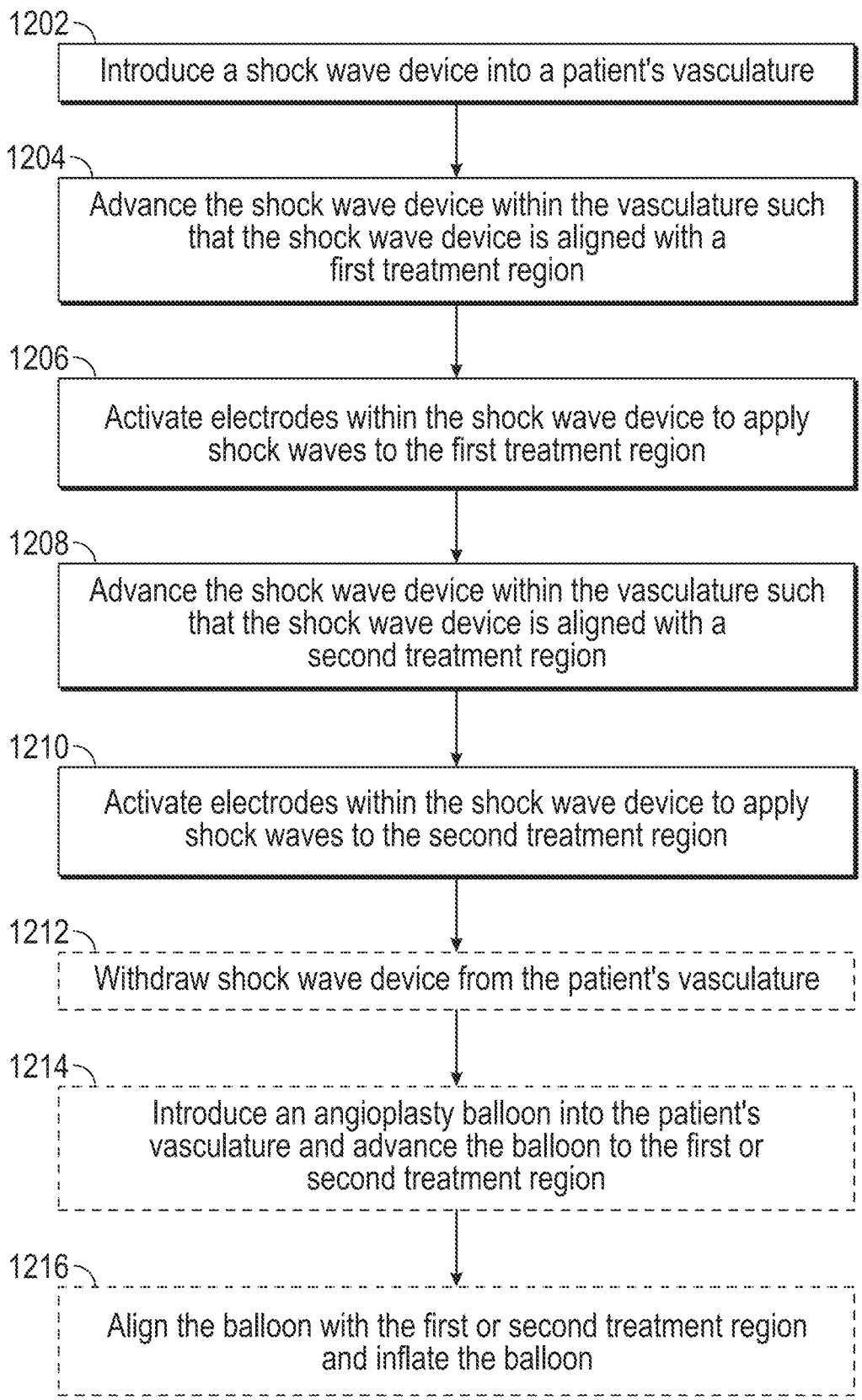
FIG. 12 is a flowchart representation of a method for delivering shock waves to treat vascular plaques.

FIG. 12 is a flowchart representation of a method for delivering shock waves to treat vascular plaques. In one exemplary method, such as is depicted in FIG. 12, a shock wave device is introduced into a patient's vasculature (1202). The shock wave device is advanced within the vasculature such that the shock wave device is aligned with a first treatment region (1204). Once the shock wave device is in position, electrodes within the shock wave device are activated to apply shock waves to the first treatment region in the patient's vasculature (1206). The shock wave device may then be advanced further within the patient's vasculature to a second treatment region (1208), and the electrodes may be activated again to apply shock waves to the second treatment region (1210). After applying shock waves to the first or second treatment regions, the shock wave device may be withdrawn from the patient's vasculature (1212). An angioplasty balloon may then be introduced into the patient's vasculature and advanced to the first or second treatment regions (1214). The angioplasty balloon may then be aligned with the first or second treatment region and inflated (1216). In this way, conventional angioplasty balloon treatments may be applied to the treatment regions after the shock wave treatments are applied.

Figure 13:
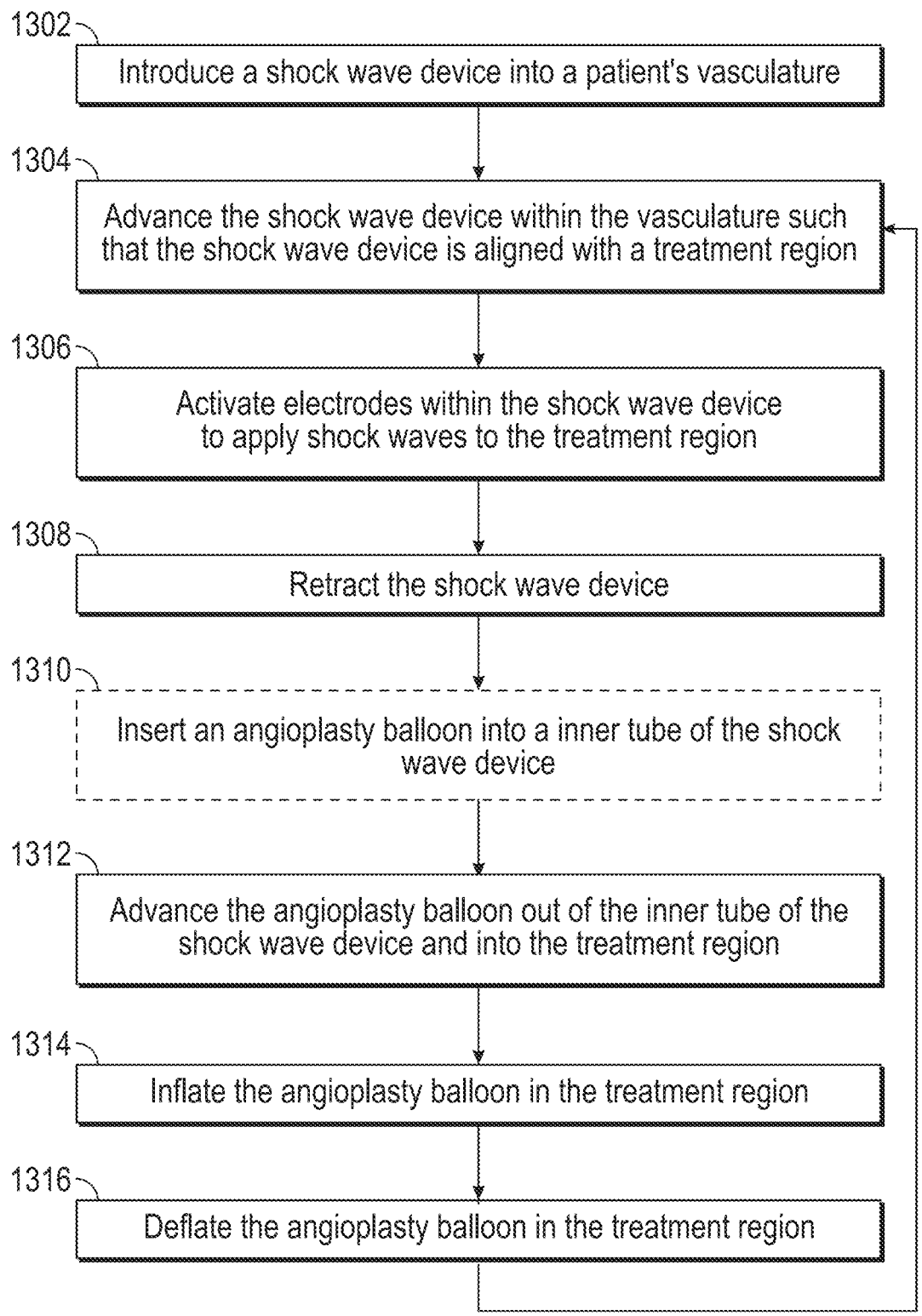
FIG. 13 is a flowchart representation of another method for delivering shock waves to treat vascular plaques

FIG. 13 is a flowchart representation of another method for delivering shock waves to treat vascular plaques. In one exemplary method, such as is depicted in FIG. 13, a shock wave device is introduced into a patient's vasculature (1302). The shock wave device is advanced within the vasculature such that the shock wave device is aligned with a treatment region (1304). Electrodes within the shock wave device are then activated to apply shock waves to the treatment region in the patient's vasculature (1306). The shock wave device may then be retracted from the treatment region (1308). The shock wave device may have been introduced with an angioplasty balloon already contained within an inner tube of the shock wave device. Alternatively, the angioplasty balloon may be inserted into the shock device subsequent to the shock wave device being introduced into the patient's vasculature (1310). For example, the angioplasty balloon may be inserted within the inner tube of the shock wave device through a port such as a rapid exchange port. The angioplasty balloon is then advanced out of the inner tube of the shock wave device and into the treatment region (1312), and the angioplasty balloon is inflated to increase the diameter of the vasculature in the treatment region (1314). In some examples, the angioplasty balloon may be only partially inflated. The angioplasty balloon is then deflated (1316) and steps 1304-1316 may be repeated as necessary to treat additional treatment regions in the patient's vasculature. When advancing the shock wave device to treat the additional treatment regions (1304), the deflated angioplasty balloon may be received within the inner tube of the shock wave device and carried by the shock wave device. Alternatively, the angioplasty balloon may be advanced to the additional treatment regions prior to advancing the shock wave device, such as described in reference to FIG. 14. In some examples the used angioplasty balloon may be removed from the patient's vasculature, and a new angioplasty balloon may be inserted (1310) to treat the additional treatment regions.

Figure 14:
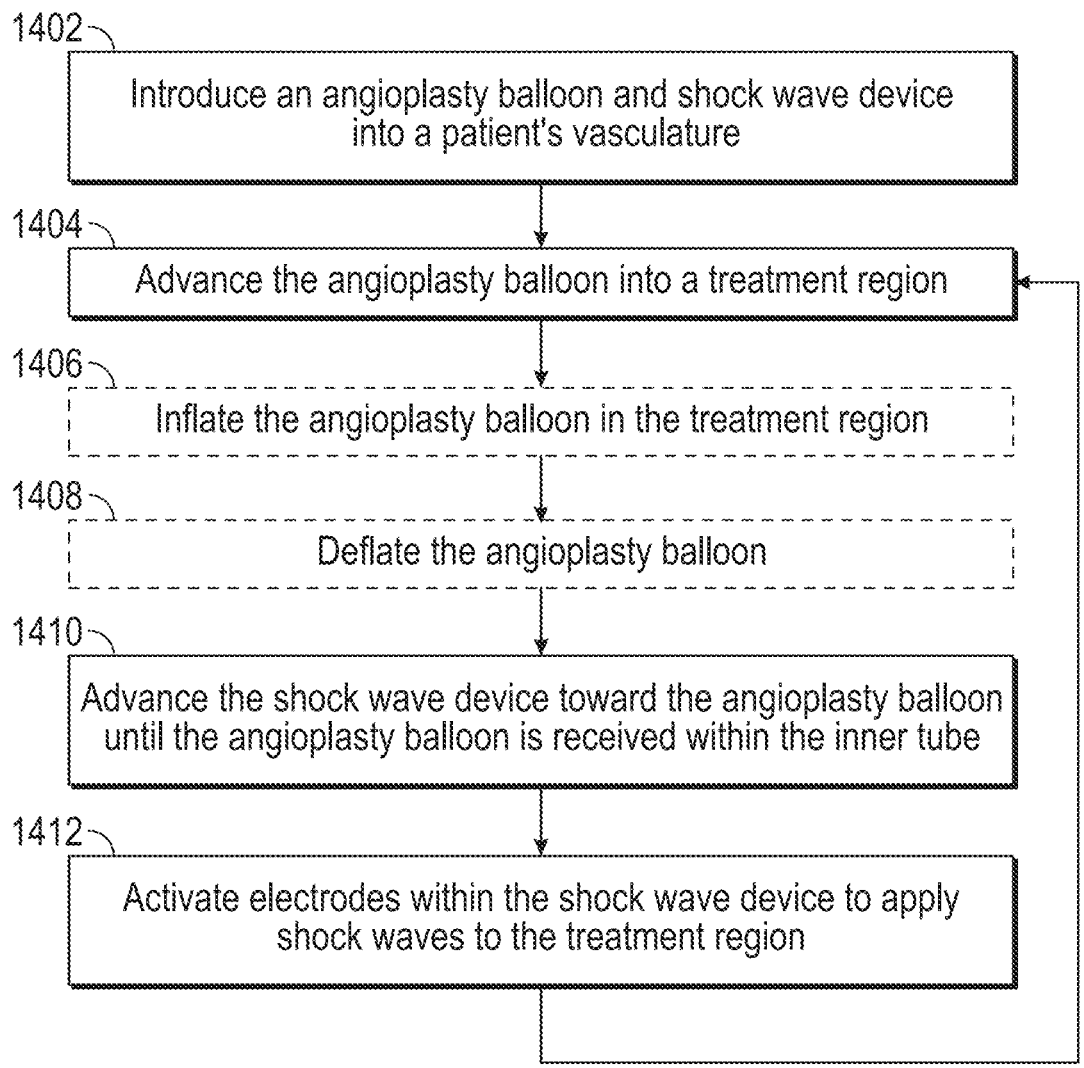
FIG. 14 is a flowchart representation of yet another method for delivering shock waves to treat vascular plaques.

FIG. 14 is a flowchart representation of another method for delivering shock waves to treat vascular plaques. In one exemplary method, such as is depicted in FIG. 14, an angioplasty balloon and shock wave device are introduced into a patient's vasculature (1402). The angioplasty balloon is advanced within the vasculature into a treatment region (1404). The shock wave device may follow the angioplasty balloon toward the treatment region. If necessary, the angioplasty balloon may then be inflated to increase the diameter of the vasculature in the treatment region (1406). In some examples, the angioplasty balloon may be only partially inflated. The angioplasty balloon may then be deflated (1408) and the shock wave device is advanced toward the angioplasty balloon until the angioplasty balloon is received within an inner tube of the shock wave device (1410). In this way, the angioplasty balloon may act as a guide for aligning the shock wave device with the treatment region. Electrodes within the shock wave device are then activated to apply shock waves to the treatment region in the patient's vasculature (1412). Steps 1404-1412 may be repeated as necessary to treat additional treatment regions in the patient's vasculature. When the angioplasty balloon is advanced into the additional treatment regions (1404), the shock wave device may remain in place while the angioplasty balloon exits the inner tube of the shock wave device and advances. The angioplasty balloon may then again act as a guide for aligning the shock wave device with the additional treatment regions.

Figure 15:
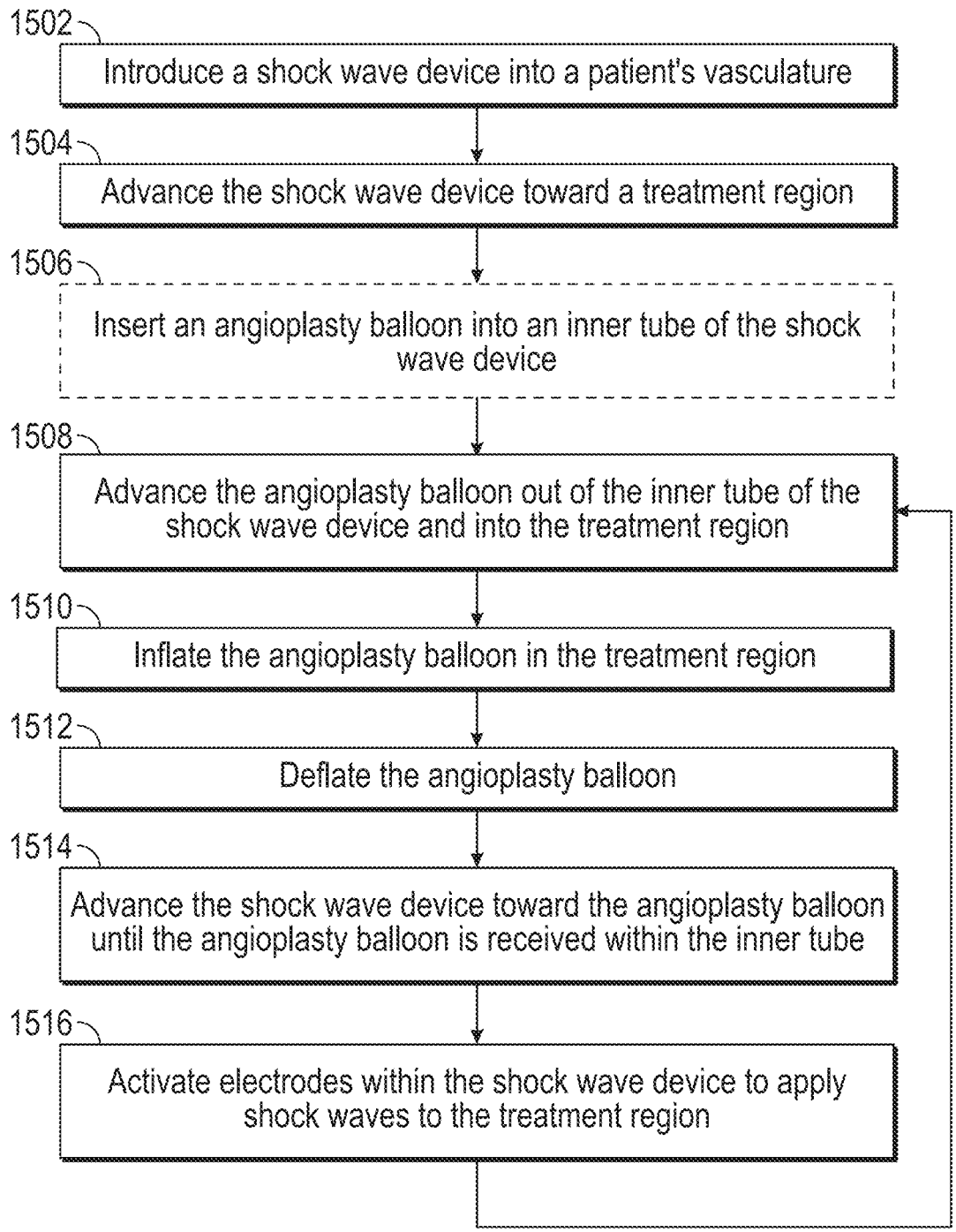
FIG. 15 is a flowchart representation of yet another method for delivering shock waves to treat vascular plaques.

FIG. 15 is a flowchart representation of another method for delivering shock waves to treat vascular plaques. In one exemplary method, such as is depicted in FIG. 15, a shock wave device is introduced into a patient's vasculature (1502). The shock wave device is advanced within the vasculature toward a treatment region (1504). The shock wave device may have been introduced with an angioplasty balloon already contained within an inner tube of the shock wave device. Alternatively, the angioplasty balloon may be inserted into the shock device subsequent to the shock wave device being introduced into the patient's vasculature (1506). For example, the angioplasty balloon may be inserted within the inner tube of the shock wave device through a port such as a rapid exchange port. The angioplasty balloon is then advanced out of an inner tube of the shock wave device and into the treatment region (1508). The angioplasty balloon is then inflated to increase the diameter of the vasculature in the treatment region (1510). In some examples, the angioplasty balloon may be only partially inflated. The angioplasty balloon is then deflated (1512) and the pair of concentric tubes are advanced toward the angioplasty balloon until the angioplasty balloon is received within the inner tube (1514). Electrodes within the shock wave device are then activated to apply shock waves to the treatment region in the patient's vasculature (1516). Steps 1508-1516 may be repeated as necessary to treat additional treatment regions in the patient's vasculature.

In the prior art devices as described in U.S. Pat. Nos. 8,956,371 and 9,999,788, cited above, the electrode pairs are positioned within the angioplasty balloon. In use, the prior art catheter carrying a deflated angioplasty balloon is advanced within the vessel to the area to be treated. The balloon is then pressurized to expand and dilate the balloon. Thereafter, the shock waves are generated within the balloon.

As discussed above, in the subject invention, the use of the dilation balloon is decoupled from the hardware used to deliver the shock waves. In the present invention, a conventional, off the shelf angioplasty balloon catheter could be deployed to partially enlarge the opening in the vessel. Thereafter, the concentric tube structure carrying the electrodes is advanced to the region to be treated. The concentric tube structure is filled with fluid, but does not have to be pressurized in the same manner as a dilating balloon. The wall of the outer tube of the current design can be thicker and less flexible than the wall of an angioplasty balloon. The outer tube can be stronger and less costly since there is no need or intent to dilate the outer tube or the vessel during shock wave treatment. The outer diameter of the outer tubes remains constant throughout the procedure.

As discussed above, in some instances, the size of the vessel in the region being treated may be sufficient to receive the concentric tube structure without dilation. In such a case, the region can be treated with shock waves generated within the concentric tubes to crack calcium deposits. Thereafter, a separate catheter carrying a folded angioplasty balloon can be advanced into the vessel through the concentric tubes. The angioplasty balloon is then pressurized sufficient to expand the vessel. Since the calcium has already been cracked, the pressure needed for this expansion stage (e.g. four to six atmospheres) would be less than if the calcium had not already been cracked.

As also discussed above, a method is envisioned wherein an angioplasty balloon is first used to open the vessel sufficient to receive the concentric tubes. The region is then treated by shock waves. Thereafter, a second pass with the same or different angioplasty balloon is made to full expand the vessel.

The subject method allows the physician to use multiple balloons of different sizes during a procedure. For example, at the start of a procedure, the physician might first use a smaller angioplasty balloon and then during the procedure swap out the first balloon in favor of a second, larger angioplasty balloon. Once the physician has sufficiently dilated the vessel, the concentric tubes carrying the electrodes are advanced to the treatment zone and the shock wave treatment is begun.

In all cases, the physician is able to use off the shelf angioplasty balloon catheters which are lower in cost and more familiar to the physician.

While this invention has been particularly shown and described with references to embodiments thereof, it will be understood by those skilled in the art that various changes in form and details may be made therein without departing from the scope of the invention. For all of the embodiments described above, the steps of the methods need not be performed sequentially.

What is claimed is:

1. A device for treating vascular plaques, comprising:
 a pair of elongated, flexible concentric tubes comprising an inner tube and an outer tube, wherein:
  the pair of concentric tubes have a fluid input end and a treatment end,
  the fluid input end is located near a proximal end of the pair of concentric tubes,
  the treatment end is located near a distal end of the pair of concentric tubes, the inner tube and the outer tube are connected together at the treatment end to form a fluid seal, and at least a portion of the volume between the inner tube and the outer tube is fillable with a conductive fluid via the fluid input end and wherein the tubes are configured such that when the volume between the inner and outer tubes is filled with conductive fluid the diameter of the outer tube does not change; and at least two electrodes positioned between the inner tube and the outer tube, the at least two electrodes being electrically connectable to a voltage source and configured to generate shock waves in the conductive fluid in response to voltage pulses.

2. The device of claim 1, wherein the pair of concentric tubes are carried by a guide wire.

3. The device of claim 1, further comprising:
a treatment appliance located within the inner tube and configured to be advanced out of the inner tube.

4. The device of claim 3, wherein the treatment appliance comprises an angioplasty balloon.

5. The device of claim 1, further comprising a fluid source and a fluid pump, the fluid pump being configured to deliver fluid from the fluid source to the fluid input end of the pair of concentric tubes.

6. The device of claim 1, wherein the at least two electrodes comprise:
a first inner electrode disposed at a first location adjacent to an outer surface of the inner tube; and
an outer electrode circumferentially disposed around the inner tube, the outer electrode having a first aperture aligned with the first inner electrode, wherein the first inner electrode and the outer electrode are separated by an insulating sheath, the insulating sheath having a second aperture coaxially aligned with the first aperture in the outer electrode so that when a voltage is applied across the electrodes, a first shock wave will be initiated from the first location.

7. The device of claim 6, wherein the size of the first aperture in the outer electrode is larger than the size of the second aperture in the insulating sheath.

8. The device of claim 6, further comprising a first wire connected to the first inner electrode and a second wire connected to the outer electrode, wherein the inner tube has first and second grooves that extend along the length of the inner tube, and the first wire is slidably disposed within the first groove and the second wire is slidably disposed within the second groove.

9. The device of claim 1, wherein the at least two electrodes comprise:
a first inner electrode disposed at a first location adjacent to an outer surface of the inner tube; and
an outer electrode circumferentially disposed around the inner tube.

10. The device of claim 9, further including a wire having an insulating coating and wherein a portion of the insulating coating is removed to define the first electrode.

11. The device of claim 10 wherein the outer electrode includes a cut-out region aligned with the first electrode.

* * * * *